(12) United States Patent
Lietzau et al.

(10) Patent No.: US 7,291,366 B2
(45) Date of Patent: Nov. 6, 2007

(54) CYCLOPENTA[B]NAPHTHALENE DERIVATIVES

(75) Inventors: Lars Lietzau, Darmstadt (DE); Matthias Bremer, Darmstadt (DE); Melanie Klasen-Memmer, Heuchelheim (DE); Michael Heckmeier, Hemsbach (DE)

(73) Assignee: Merck Patent GmbH, Darmstadt (DE)

( * ) Notice: Subject to any disclaimer, the term of this patent is extended or adjusted under 35 U.S.C. 154(b) by 163 days.

(21) Appl. No.: 10/524,846

(22) PCT Filed: Jul. 28, 2003

(86) PCT No.: PCT/EP03/08285

§ 371 (c)(1),
(2), (4) Date: Feb. 18, 2005

(87) PCT Pub. No.: WO2004/020375

PCT Pub. Date: Mar. 11, 2004

(65) Prior Publication Data

US 2006/0165915 A1  Jul. 27, 2006

(30) Foreign Application Priority Data

Aug. 26, 2002 (DE) ............... 102 38 999
Jun. 2, 2003 (DE) ............... 103 24 843

(51) Int. Cl.
 C09K 19/32 (2006.01)
 C07C 25/22 (2006.01)
 C07C 23/08 (2006.01)
 C07C 23/18 (2006.01)

(52) U.S. Cl. ............ 428/1.1; 252/299.62; 570/183

(58) Field of Classification Search ............. 428/1.1; 252/299.01, 299.5, 299.62, 299.61; 570/183
See application file for complete search history.

(56) References Cited

U.S. PATENT DOCUMENTS

| | | |
|---|---|---|
| 6,271,411 B1 | 8/2001 | Nifant'ev et al. |
| 6,759,103 B2 * | 7/2004 | Hornung et al. ............. 428/1.1 |
| 2003/0091756 A1 * | 5/2003 | Hornung et al. ............. 428/1.1 |
| 2004/0150633 A1 * | 8/2004 | Heckmeier et al. ......... 345/204 |

FOREIGN PATENT DOCUMENTS

| | | |
|---|---|---|
| DE | 4434974 | 4/1996 |
| DE | 10217273 | * 12/2002 |
| EP | 1223209 | 7/2002 |
| WO | WO 9846547 | 10/1998 |
| WO | WO 0246330 | 6/2002 |

OTHER PUBLICATIONS

Chemical Abstracts, vol. 122, No. 16, Apr. 17, 1995 Columbus, Ohio, US; abstract No. 201408, Yokokoji, Osamu et al: "Fluorine-containing indane derivatives and liquid crystal compositions containing same" XP002248134 & JP 06263663 (Asahi Glass Co Ltd, Japan) Sep. 20, 1994.

* cited by examiner

*Primary Examiner*—Shean C Wu
(74) *Attorney, Agent, or Firm*—Millen, White, Zelano & Branigan, P.C.

(57) ABSTRACT

The present invention relates to cyclopenta[b]naphthalene derivatives of the general formula (I) in which Z, A, n, R, $L^5$ and $L^8$ as (II) and (III) are as defined in Claim 1, to the use thereof in liquid-crystalline or mesogenic media, to liquid-crystalline or mesogenic media comprising at least one of these cyclopenta[b]naphthalene derivatives, and to electro-optical display elements containing these liquid-crystalline or mesogenic media

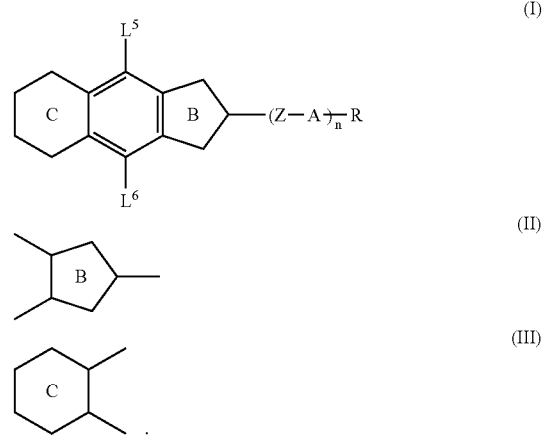

11 Claims, No Drawings

CYCLOPENTA[B]NAPHTHALENE DERIVATIVES

The present invention relates to cyclopenta[b]naphthalene derivatives, to the use thereof in liquid-crystalline or mesogenic media, to liquid-crystalline or mesogenic media comprising these derivatives, and to electro-optical display elements containing these liquid-crystalline or mesogenic media.

Liquid crystals have found widespread use since the first commercially usable liquid-crystalline compounds were found about 30 years ago. Known areas of application are, in particular, displays for watches and pocket calculators, and large display panels as used in railway stations, airports and sports arenas. Further areas of application are displays of portable computers and navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elasto-mechanical anisotropies. Depending on whether the molecules are oriented with their longitudinal axes perpendicular or parallel to the two plates of a capacitor, the latter has a different capacitance; in other words, the dielectric constant $\epsilon$ of the liquid-crystalline medium has different values for the two orientations. Substances whose dielectric constant is larger in the case of a perpendicular orientation of the longitudinal axes of the molecules to the capacitor plates than in the case of a parallel arrangement are referred to as dielectrically positive. Most liquid crystals used in conventional displays fall into this group.

Both the polarisability of the molecule and permanent dipole moments play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The incorporation of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. The orientation of the larger dipole moment along the longitudinal axis of the molecule also determines the orientation of the molecule in a liquid-crystal display in the field-free state. In the most widespread TN ("twisted nematic") cells, a liquid-crystalline layer with a thickness of only from about 5 to 10 μm is arranged between two flat glass plates, onto each of which an electrically conductive, trans-parent layer of tin oxide or indium tin oxide has been vapour-deposited as electrode. A likewise transparent alignment layer, which usually consists of a plastic (for example polyimides), is located between these films and the liquid-crystalline layer. This alignment layer serves to bring the longitudinal axes of the adjacent crystalline molecules into a preferential direction through surface forces in such a way that, in the voltage-free state, they lie uniformly on the inside of the display surface with the same orientation in a flat manner or with the same small tilt angle. Two polarisation films which only enable linear-polarised light to enter and escape are adhesively bonded to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality drops drastically under certain circumstances. For greater comfort, attempts are being made to make the angle through which the display can be tilted from the viewing direction of an observer as large as possible. Attempts have recently been made to improve the viewing-angle dependence using liquid-crystalline compounds whose dipole moment perpendicular to the longitudinal axis of the molecules is larger than that parallel to the longitudinal axis of the molecule. In the field-free state, these molecules are oriented perpendicular to the glass surface of the display. In this way, it has been possible to achieve an improvement in the viewing-angle dependence. Displays of this type are known as VA-TFT ("vertically aligned") displays.

DE 44 34 974 A1 discloses tricyclic compounds of the general formula

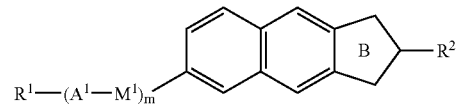

in which the symbols and indices have the following meanings:

$R^1$ is —F, —CN, —Cl, —CF$_3$ or has, independently of $R^2$, one of the meanings mentioned for $R^2$;

$R^2$ is H or a straight-chain or branched alkyl radical having from 1 to 20 carbon atoms (with or without an asymmetrical carbon atom), in which, in addition, one or more —CH$_2$— groups (but not those bonded directly to the five-membered ring) may be replaced by —O—, —S—, —CH═CH—, —C≡C—, cyclo-propane-1,2-diyl, —Si(CH$_3$)$_2$—, 1,4-phenylene, 1,4-cyclohexylene, 1,3-cyclopentylene, 1,3-cyclobutylene, 1,3-dioxane-2,5-diyl, with the proviso that oxygen atoms and sulfur atoms must not be bonded directly, and in which, in addition, one or more H atoms of the alkyl radical may be substituted by F, Cl, Br or OR$^3$, or an optically active or racemic group;

Ring B is

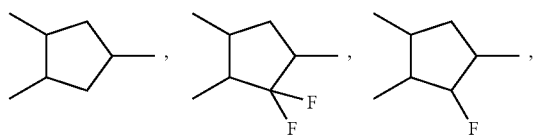

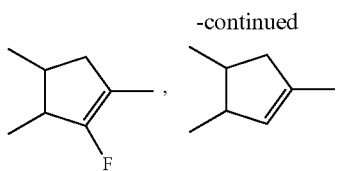

$A^1$ is 1,4-phenylene, 1,4-cyclohexylene, pyridine-2,5-diyl, pyrimidine-2,5-diyl, 1,3-thiazole-2,5-diyl, 1,3-thiazole-2,4-diyl, in which, in addition, one or more hydrogens may be substituted by F, 1,3,4-thiadiazole-2,5-diyl;

$M^1$ is a single bond, —C≡C—, —CH$_2$CH$_2$—, —O—CO—, —CO—O—, —CO—, —OCH$_2$—, —CH$_2$O— or —O—CO—O—; and m is zero or one.

However, the Δε of the compounds disclosed in this document is not sufficient to ensure satisfactory properties, for example in VA-TFT displays.

Development in the area of liquid-crystalline materials is far from complete. In order to improve the properties of liquid-crystalline display elements, attempts are constantly being made to develop novel compounds which enable such displays to be optimised.

An object of the present invention was to provide compounds having advantageous properties for use in liquid-crystalline media.

This object is achieved in accordance with the invention by cyclopenta[b]-naphthalene derivatives of the general formula (I)

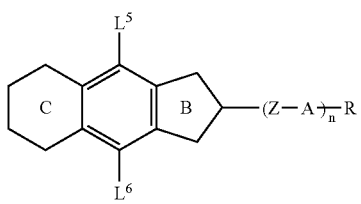
(I)

in which:

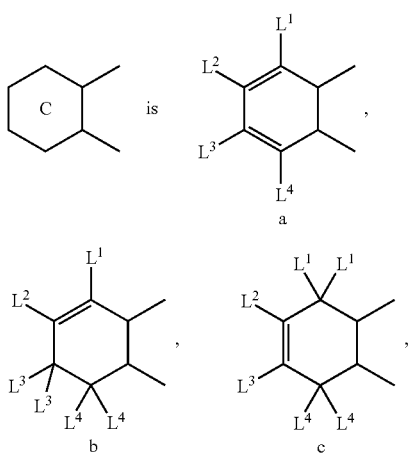

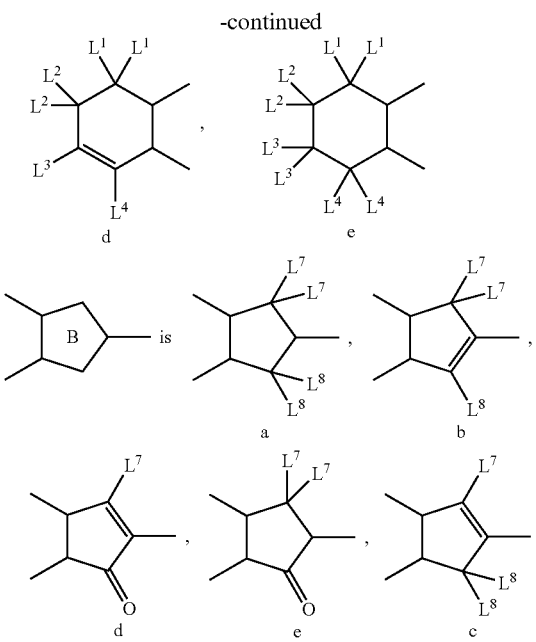

Z is in each case, independently of one another, a single bond, a double bond, —CF$_2$O—, —OCF$_2$—, —CH$_2$CH$_2$—, —CF$_2$CF$_2$—, —C(O)O—, —OC(O)—, —CH$_2$O—, —OCH$_2$—, —CF═CH—, —CH═CF—, —CF═CF—, —CH═CH—, —CH═CH— or —C≡C—, A is in each case, independently of one another, 1,4-phenylene, in which ═CH— may be replaced once or twice by ═N—, and which may be monosubstituted to tetrasubstituted, independently of one another, by halogen (—F, —Cl, —Br, —I), —CN, —CH$_3$, —CH$_2$F, —CHF$_2$, —CF$_3$, —OCH$_3$, —OCH$_2$F, —OCHF$_2$ or —OCF$_3$, 1,4-cyclohexylene, 1,4-cyclohexenylene or 1,4-cyclohexadienylene, in which —CH$_2$— may be replaced once or twice, independently of one another, by —O— or —S— in such a way that heteroatoms are not directly adjacent, and which may be monosubstituted or polysubstituted by halogen, or is 1,3-cyclobutylene or bicyclo[2.2.2]octane, R is hydrogen, an alkyl, alkoxy, alkenyl or alkynyl radical having from 1 to 15 or 2 to 15 carbon atoms respectively which is unsubstituted, monosubstituted by —CF$_3$ or at least monosubstituted by halogen, where, in addition, one or more CH$_2$ groups in these radicals may each, independently of one another, be replaced by —O—, —S—, —CO—, —COO—, —OCO— or —OCO—O— in such a way that heteroatoms are not directly adjacent, halogen, —CN, —SCN, —NCS, —SF$_5$, —CF$_3$, —OCF$_3$, —OCHF$_2$ or —OCH$_2$F, n is 0, 1, 2 or 3, and $L^1$-$L^8$ are each, independently of one another, hydrogen, an alkyl, alkoxy, alkenyl or alkynyl radical having from 1 to 15 or 2 to 15 carbon atoms respectively which is unsubstituted or at least mono-substituted by halogen, where, in addition, one or more CH$_2$ groups in these radicals may each, independently of one another, be replaced by —O—, —S—, —CO—, —COO—, —OCO— or —OCO—O— in such a way that heteroatoms are not directly adjacent, halogen, —CN, —SCN, —NCS, —SF$_5$, —CF$_3$, —OCF$_3$, —OCHF$_2$, —OCH$_2$F or -(Z-A-)$_n$—R.

A further object of the present invention was to provide liquid-crystalline compounds, in particular for use in VA-TFT displays.

This object is achieved in accordance with the invention by the provision of cyclopenta[b]naphthalene derivatives of negative Δε.

The present invention thus relates, in particular, to cyclopenta[b]naphthalene derivatives of the general formulae (II) to (VI)

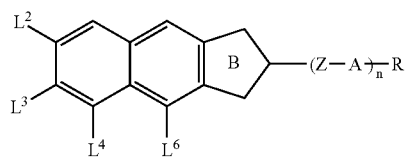
(II)

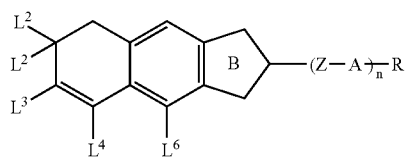
(III)

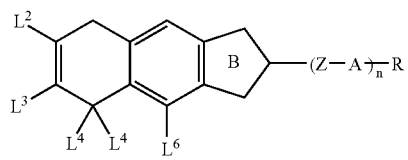
(IV)

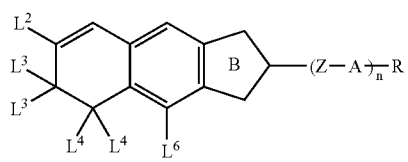
(V)

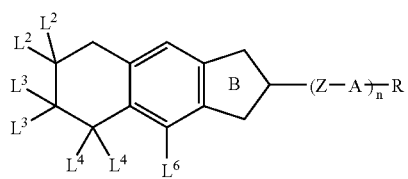
(VI)

in which:

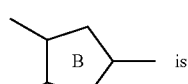 is

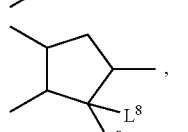
a, b, c

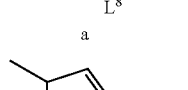
d, e, f

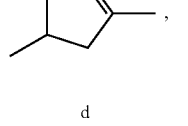

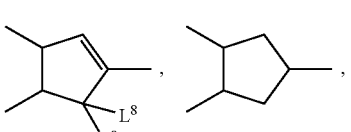
g, h

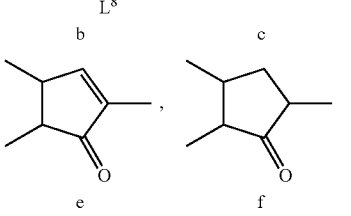
i, j

Z is in each case, independently of one another, a single bond, a double bond, —CF$_2$O—, —OCF$_2$—, —CH$_2$CH$_2$—, —CF$_2$CF$_2$—, —C(O)O—, —OC(O)—, —CH$_2$O—, —OCH$_2$—, —CF=CH—, —CH=CF—, —CF=CF—, —CH=CH— or —C≡C—, A is in each case, independently of one another, 1,4-phenylene, in which =CH— may be replaced once or twice by =N—, and which may be monosubstituted to tetrasubstituted, independently of one another, by halogen (—F, —Cl, —Br, —I), —CN, —CH$_3$, —CH$_2$F, —CHF$_2$, —CF$_3$, —OCH$_3$, —OCH$_2$F, —OCHF$_2$ or —OCF$_3$, 1,4-cyclohexylene, 1,4-cyclohexenylene or 1,4-cyclohexadienylene, in which —CH$_2$— may be replaced once or twice, independently of one another, by —O— or —S— in such a way that heteroatoms are not directly adjacent, and which may be monosubstituted or polysubstituted by halogen, or is 1,3-cyclobutylene or bicyclo[2.2.2]octane, R is hydrogen, an alkyl, alkoxy, alkenyl or alkynyl radical having from 1 to 15 or 2 to 15 carbon atoms respectively which is unsubstituted, monosubstituted by —CF$_3$ or at least monosubstituted by halogen, where, in addition, one or more CH$_2$ groups in these radicals may each, independently of one another, be replaced by —O—, —S—, —CO—, —COO—, —OCO— or —OCO—O— in such a way that heteroatoms are not directly adjacent, halogen, —CN, —SCN, —NCS, —SF$_5$, —CF$_3$, —OCF$_3$, —OCHF$_2$ or —OCH$_2$F, L$^2$, L$^3$ and L$^8$ are each, independently of one another, hydrogen, an alkyl, alkoxy, alkenyl or alkynyl radical having from 1 to 15 or 2 to 15 carbon atoms respectively which is unsubstituted or at least mono-substituted by halogen, where, in addition, one or more CH$_2$ groups in these radicals may each, independently of one another, be replaced by —O—, —S—, —CO—, —COO—, —OCO— or —OCO—O— in such a way that heteroatoms are not directly adjacent, halogen, —CN, —SCN, —NCS, —SF$_5$, —CF$_3$, —OCF$_3$, —OCHF$_2$, —OCH$_2$F or -(Z-A-)$_n$-R, L$^4$ and L$^6$ are each, independently of one another, hydrogen, an alkyl, alkoxy, alkenyl or alkynyl radical having from 1 to 15 or 2 to 15 carbon atoms respectively which is at least monosubstituted by halogen, where, in addition, one or more CH$_2$ groups in these radicals may each, independently of one another, be replaced by —O—, —S—, —CO—, —COO—, —OCO— or —OCO—O— in such a way that hetero-atoms are not directly adjacent, halogen, —CN, —SF$_5$, —SCN, —NCS, —CF$_3$, —OCF$_3$, —OCHF$_2$ or —OCH$_2$F, preferably with the proviso that L$^4$ and L$^6$ cannot simultaneously be hydrogen, and n is 0, 1, 2 or 3.

Preference is given to cyclopenta[b]naphthalene derivatives of the general formulae (II), (III), (V) and (VI), and particular preference is given to cyclopenta[b]naphthalene derivatives of the general formulae (II) and (VI).

The compounds all have negative Δε and are therefore suitable, in particular, for use in VA-TFT displays. The compounds according to the invention preferably have a Δε of <−2 and particularly preferably a Δε of <−5. They exhibit very good compatibility with the conventional substances used in liquid-crystal mixtures for displays.

The substituents, preferably fluorine substituents, in the naphthalene structure and the electronegative atoms in ring B generate a dipole moment perpendicular to the longitudinal axis of the molecules, which can, if desired, be further strengthened by suitable substituents in the wing units -(Z-A-)$_n$-R. In the field-free state, the compounds of the formulae (II) to (VI) orient themselves with their longitudinal axis of the molecules perpendicular to the treated or coated glass surface of the display.

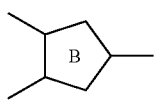

in the general formulae (II) to (VI) are preferably

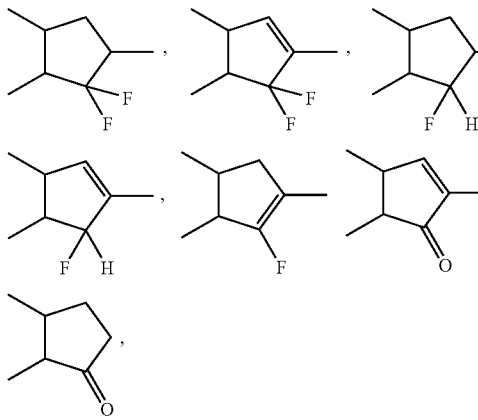

particularly preferably

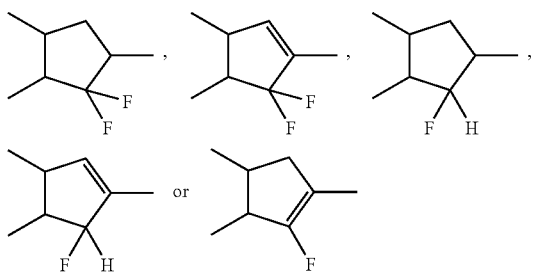

and in particular

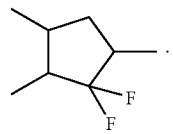

In the general formulae (II) to (VI), A are preferably, independently of one another, optionally substituted 1,4-phenylene, optionally substituted 1,4-cyclohexylene, in which —CH$_2$— may be replaced once or twice by —O—, or optionally substituted 1,4-cyclohexenylene.

A are particularly preferably, independently of one another,

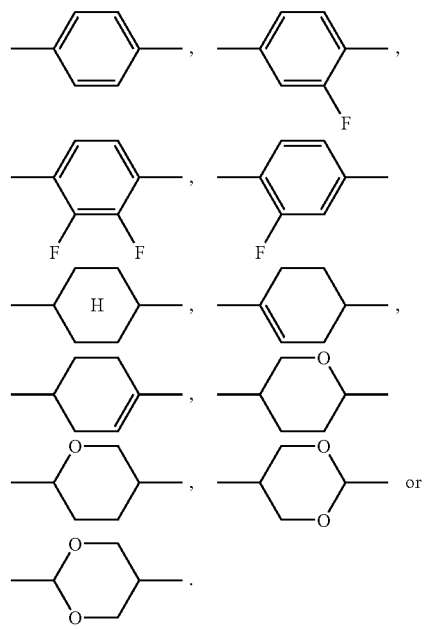

Preferred groups Z in the compounds of the general formulae (II) to (VI) are each, independently of one another, a single bond, —CF$_2$O—, —OCF$_2$—, —CF$_2$CF$_2$—, —CH=CH—, —CF=CH—, —CH=CF— or —CF=CF—, particularly preferably a single bond, —CF$_2$O—, —OCF$_2$—, —CF$_2$CF$_2$—, —CF=CH—, —CH=CF— or —CF=CF—.

R, L$^2$ and L$^3$ in the general formulae (II) to (VI) may each, independently of one another, be an alkyl radical and/or an alkoxy radical having from 1 to 15 carbon atoms, which may be straight-chain or branched. It is preferably straight-chain, has 1, 2, 3, 4, 5, 6 or 7 carbon atoms and accordingly is preferably methyl, ethyl, propyl, butyl, pentyl, hexyl, heptyl, methoxy, ethoxy, propoxy, butoxy, pentoxy, hexyloxy or heptyloxy.

R, L$^2$ and L$^3$ may each, independently of one another, be oxaalkyl, preferably straight-chain 2-oxapropyl(=methoxymethyl), 2-(=ethoxymethyl) or 3-oxabutyl(=methoxyethyl), 2-, 3- or 4-oxapentyl, 2-, 3-, 4- or 5-oxahexyl, 2-, 3-, 4-, 5- or 6-oxaheptyl.

R, L$^2$ and L$^3$ may each, independently of one another, be an alkenyl radical having from 2 to 15 carbon atoms, which may be straight-chain or branched. It is preferably straight-chain and has from 2 to 7 carbon atoms. Accordingly, it is preferably vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl.

R, $L^2$ and $L^3$ may each, independently of one another, be an alkyl radical having from 1 to 15 carbon atoms in which one $CH_2$ group has been replaced by —O— and one has been replaced by —CO—, where these are preferably adjacent. This thus contains an acyloxy group —CO—O— or an oxycarbonyl group —O—CO—. This is preferably straight-chain and has from 2 to 6 carbon atoms.

R, $L^2$ and $L^3$ may each, independently of one another, be an alkyl radical having from 1 to 15 carbon atoms in which one $CH_2$ group has been replaced by unsubstituted or substituted —CH=CH— and an adjacent $CH_2$ group has been replaced by CO or CO—O or O—CO, where this may be straight-chain or branched. It is preferably straight-chain and has from 4 to 13 carbon atoms.

R, $L^2$ and $L^3$ may each, independently of one another, be an alkyl radical having from 1 to 15 carbon atoms or alkenyl radical having from 2 to 15 carbon atoms, each of which is monosubstituted by —CN or —$CF_3$, where these are preferably straight-chain. The substitution by —CN or —$CF_3$ is possible in any desired position.

R, $L^2$ and $L^3$ may each, independently of one another, be an alkyl radical in which two or more $CH_2$ groups have been replaced by —O— and/or —CO—O—, where this may be straight-chain or branched. It is preferably branched and has from 3 to 12 carbon atoms.

R, $L^2$, $L^3$, $L^4$ and $L^6$ may each, independently of one another, be an alkyl radical having from 1 to 15 carbon atoms or alkenyl radical having from 2 to 15 carbon atoms, each of which is at least monosubstituted by halogen, where these radicals are preferably straight-chain and halogen is preferably —F or —Cl. In the case of polysubstitution, halogen is preferably —F. The resultant radicals also include perfluorinated radicals, such as —$CF_3$. In the case of monosubstitution, the fluorine or chlorine substituent can be in any desired position, but is preferably in the ω-position.

R in the general formulae (II) to (VI) is particularly preferably an alkyl radical, alkoxy radical or alkenyl radical having from 1 to 7 or 2 to 7 carbon atoms respectively.

$L^2$ and $L^3$ in the general formulae (II) to (VI) is preferably hydrogen, an alkyl radical, alkoxy radical or alkenyl radical having from 1 to 7 or 2 to 7 carbon atoms respectively or a halogen, particularly preferably hydrogen, an alkoxy radical having from 1 to 7 carbon atoms, fluorine or chlorine, and in particular fluorine.

$L^4$ and $L^6$ in the general formulae (II) to (VI) is preferably hydrogen, an alkyl radical, alkoxy radical or alkenyl radical having from 1 to 7 or 2 to 7 carbon atoms respectively, each of which is at least monosubstituted by halogen, or a halogen, particularly preferably —$CF_3$, fluorine or chlorine, and in particular fluorine.

$L^8$ in the general formulae (II) to (VI) is preferably fluorine.

Preferred compounds of the general formulae (II) to (VI) have no, one or two wing units ZA, i.e. n=0, 1 or 2, particularly preferably n=1.

A further object of the present invention was to provide compounds, in particular for use in mesogenic control media, where these control media are employed, in particular, in electro-optical light-control elements which are operated at a temperature at which the mesogenic control medium in the unaddressed state is in the isotropic phase.

This object is achieved in accordance with the invention by the provision of cyclopenta[b]naphthalene derivatives of positive Δε.

The present invention thus relates, in particular, to cyclopenta[b]naphthalene derivatives of the general formulae (VII) to (XI)

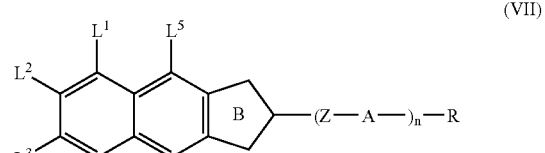
(VII)

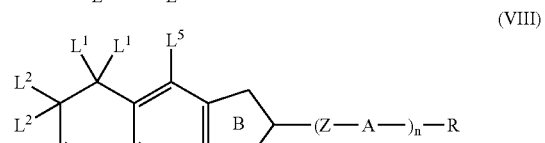
(VIII)

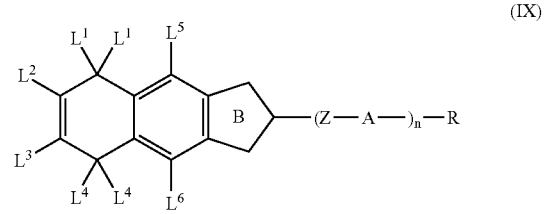
(IX)

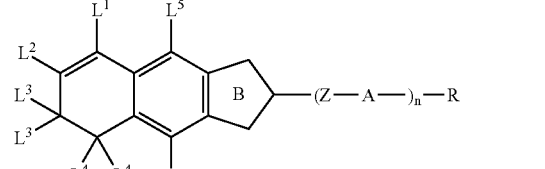
(X)

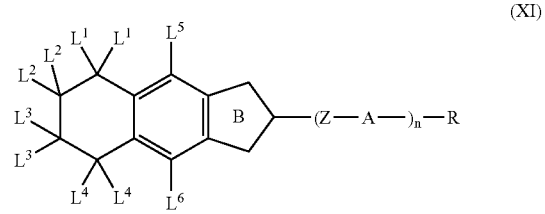
(XI)

in which Z, A, R, n, $L^1$ to $L^8$ and

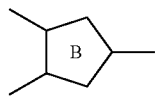

have the meanings indicated in relation to the formula (I).

Preference is given to cyclopenta[b]naphthalene derivatives of the general formulae (VII) and (XI), and particular preference is given to cyclopenta[b]-naphthalene derivatives of the general formula (VII).

The compounds of the formulae (VII) to (XI) all have positive Δε. The compounds of the formulae (VII) to (XI) according to the invention preferably have a Δε of >+10, particularly preferably a Δε of >+15 and in particular a Δε of >+20. They exhibit very good compatibility with the conventional substances used in mesogenic control media.

The cyclopenta[b]naphthalene derivatives of the general formula (VII) preferably have the following structural formulae:

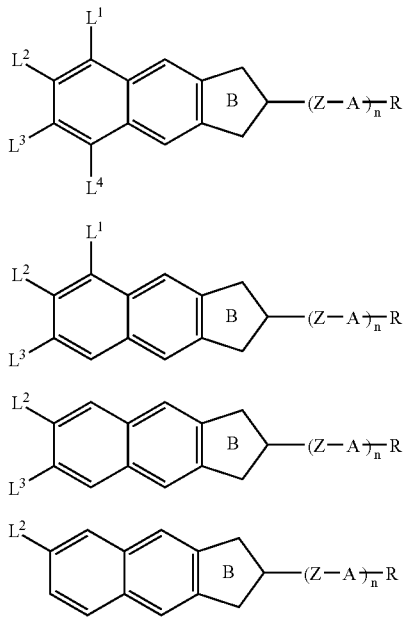

(VIIa)
(VIIb)
(VIIc)
(VIId)

where the structural formulae (VIIa) and (VIIc) are particularly preferred.

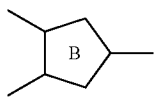

in the general formulae (VII) to (XI) are preferably particularly preferably

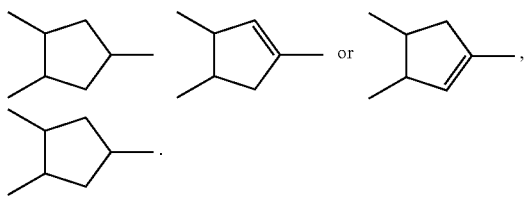

In the general formulae (VII) to (XI), A are preferably, independently of one another, optionally substituted 1,4-phenylene, optionally substituted 1,4-cyclohexylene, in which —$CH_2$— may be replaced once or twice by —O—, or optionally substituted 1,4-cyclohexenylene.

A are particularly preferably, independently of one another,

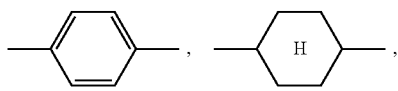

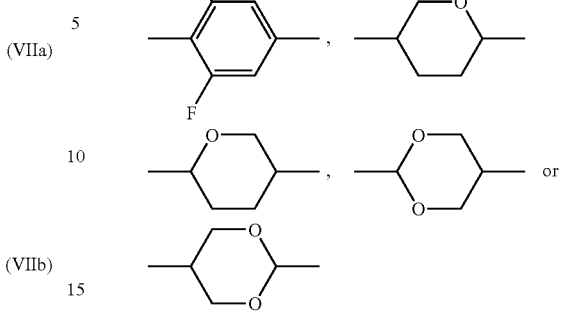

Preferred groups Z in the compounds of the general formulae (VII) to (XI) are each, independently of one another, a single bond, —$CF_2O$—, —$OCF_2$—, —$CF_2CF_2$—, —CH=CH—, —CF=CH—, —CH=CF— or —CF=CF—, particularly preferably a single bond, —$CF_2O$—, —$OCF_2$—, —$CF_2CF_2$— or —CF=CF—.

R and $L^1$ to $L^8$ in the general formulae (VII) to (XI) may each, independently of one another, be an alkyl radical and/or an alkoxy radical having from 1 to 15 carbon atoms, which may be straight-chain or branched. It is preferably straight-chain, has 1, 2, 3, 4, 5, 6 or 7 carbon atoms and accordingly is preferably methyl, ethyl, propyl, butyl, pentyl, hexyl, heptyl, methoxy, ethoxy, propoxy, butoxy, pentoxy, hexoxy or heptoxy.

R and $L^1$ to $L^8$ in the general formulae (VII) to (XI) may each, independently of one another, be oxaalkyl, preferably straight-chain 2-oxapropyl(=methoxymethyl), 2-(=ethoxymethyl) or 3-oxabutyl(=methoxyethyl), 2-, 3- or 4-oxapentyl, 2-, 3-, 4- or 5-oxahexyl, 2-, 3-, 4-, 5- or 6-oxaheptyl.

R and $L^1$ to $L^8$ in the general formulae (VII) to (XI) may each, independently of one another, be an alkenyl radical having from 2 to 15 carbon atoms, which may be straight-chain or branched. It is preferably straight-chain and has from 2 to 7 carbon atoms. Accordingly, it is preferably vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-eny R and $L^1$ to $L^8$ in the general formulae (VII) to (XI) may each, independently of one another, be an alkyl radical having from 1 to 15 carbon atoms in which one $CH_2$ group has been replaced by —O— and one has been replaced by —CO—, where these are preferably adjacent. This thus contains an acyloxy-group —CO—O— or an oxycarbonyl group —O—CO—. This is preferably straight-chain and has from 2 to 6 carbon atoms.

R and $L^1$ to $L^8$ in the general formulae (VII) to (XI) may each, independently of one another, be an alkyl radical having from 1 to 15 carbon atoms in which one $CH_2$ group has been replaced by unsubstituted or substituted —CH=CH— and an adjacent $CH_2$ group has been replaced by CO or CO—O or O—CO, where this may be straight-chain or branched. It is preferably straight-chain and has from 4 to 13 carbon atoms.

R and $L^1$ to $L^8$ in the general formulae (VII) to (XI) may each, independently of one another, be an alkyl radical having from 1 to 1.5 carbon atoms or alkenyl radical having from 2 to 15 carbon atoms, each of which is monosubstituted by —CN or —$CF_3$, where these are preferably straight-chain. The substitution by —CN or —CF$_3$ is possible in any desired position.

R and $L^1$ to $L^8$ in the general formulae (VII) to (XI) may each, independently of one another, be an alkyl radical in which two or more CH$_2$ groups have been replaced by —O— and/or —CO—O—, where this may be straight-chain or branched. It is preferably branched and has from 3 to 12 carbon atoms.

R and $L^1$ to $L^8$ in the general formulae (VII) to (XI) may each, independently of one another, be an alkyl radical having from 1 to 15 carbon atoms or alkenyl radical having from 2 to 15 carbon atoms, each of which is at least monosubstituted by halogen, where these radicals are preferably straight-chain and halogen is preferably —F or —Cl. In the case of polysubstitution, halogen is preferably —F. The resultant radicals also include perfluorinated radicals, such as —CF$_3$. In the case of monosubstitution, the fluorine or chlorine substituent can be in any desired position, but is preferably in the ω-position.

R in the general formulae (VII) to (XI) is particularly preferably an alkyl radical, alkoxy radical or alkenyl radical having from 1 to 7 or 2 to 7 carbon atoms respectively, in particular an alkyl radical having from 1 to 7 carbon atoms.

$L^2$ and $L^3$ in the general formulae (VII) to (XI) is preferably, independently of one another, identical or different and is hydrogen, halogen, —CN, —SCN, —NCS, —SF$_5$, —CF$_3$, —CHF$_2$, —OCF$_3$ or —OCHF$_2$, particularly preferably hydrogen, fluorine, —CF$_3$ or —OCF$_3$. In particular, however, $L^2$ and/or $L^3$ is not hydrogen.

$L^1$ and $L^4$ in the general formulae (VII) to (XI) is preferably, independently of one another, identical or different and is hydrogen or fluorine. Particularly preferably, however, $L^1=L^4=$H or $L^1=L^4=$F.

$L^5$ and $L^6$ in the general formulae (VII) to (XI) is preferably hydrogen.

Particular preference is given to compounds of the general formulae (VII) to (XI) in which L1=L2=L3=L4=F and L5=L6=H.

Preferred compounds of the general formulae (VII) to (XI) have no, one or two wing units ZA, i.e. n=0, 1 or 2, particularly preferably n=1.

The compounds of the general formulae (I), (II) to (VI) and (VII) to (XI) are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for the said reactions. Use can be made here of variants known per se, which are not mentioned here in greater detail.

If desired, the starting materials can also be formed in situ by not isolating them from the reaction mixture, but instead immediately converting them further into the compounds of the general formulae (I) to (XI).

The syntheses of various polysubstituted naphthalene derivatives which are used to build up the five-membered ring are described by way of example in the examples. The starting substances are obtainable by generally accessible literature procedures or commercially. The reactions described should likewise be regarded as known from the literature.

An illustrative synthesis for building up the five-membered ring is shown below. The synthesis can be adapted to the particular desired compounds of the general formulae (I) to (XI) through the choice of suitable starting materials.

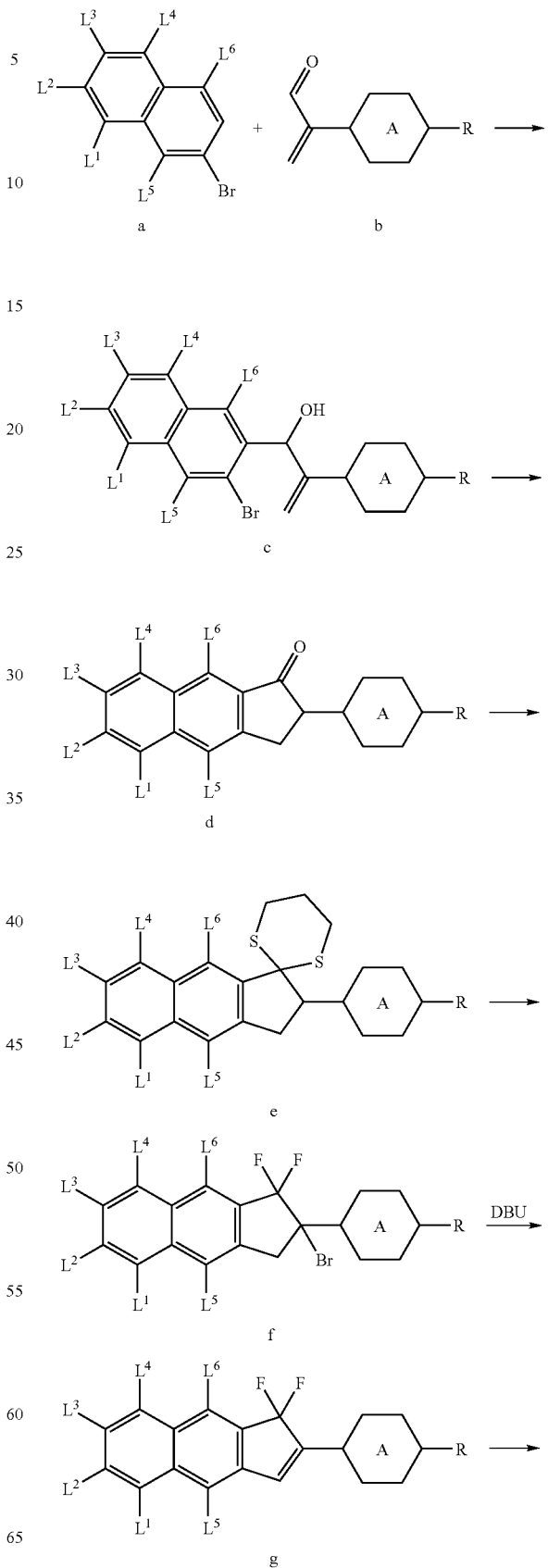

-continued

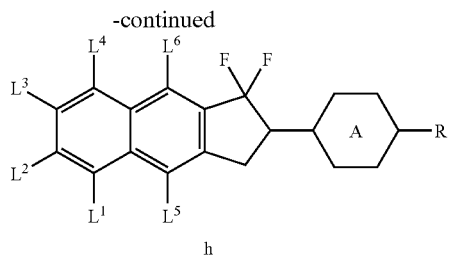

Starting from the 3-bromonaphthalene a, reaction with an α,β-unsaturated aldehyde b in the presence of lithium diisopropylamide (LDA) gives compound c. This reacts with palladium catalysis in the presence of triethylamine with ring closure to give the ketone d. From the ketone d and 1,3-propanedithiol in the presence of $BF_3$/diethyl ether, the corresponding dithiane e is obtained. This is reacted with 1,3-dibromo-5,5-dimethylhydantoin (DBH) and HF in pyridine to give the cyclopenta[b]naphthalene derivative f. Elimination of HBr in the presence of diazabicycloundecene (DBU) gives the cyclopenta[b]naphthalene derivative g. The cyclopenta[b]naphthalene derivative g is hydrogenated on the palladium/carbon catalyst in a hydrogen atmosphere to give the cyclopenta[b]naphthalene derivative h.

The reactions described should only be regarded as illustrative. The person skilled in the art can carry out corresponding variations of the syntheses described and also follow other suitable synthetic routes in order to obtain compounds of the formulae (I) to (XI).

As already mentioned, the compounds of the general formulae (I) to (XI) can be used in liquid-crystalline media.

The present invention therefore also relates to a liquid-crystalline medium comprising at least two liquid-crystalline compounds, comprising at least one compound of the general formulae (I) to (XI).

The present invention also relates to liquid-crystalline media comprising from 2 to 40, preferably from 4 to 30, components as further constituents besides one or more compounds of the formulae (I), (II), (III), (IV), (V), (VI), (VII), (VIII), (IX), (X) and/or (XI) according to the invention. These media particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclo-hexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae (1), (2), (3), (4) and (5):

R'-L-E-R"  (1)

R'-L-COO-E-R"  (2)

R'-L-OOC-E-R"  (3)

R'-L-$CH_2CH_2$-E-R"  (4)

R'-L-$CF_2O$-E-R"  (5)

In the formulae (1), (2), (3), (4) and (5), L and E, which may be identical or different, are each, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2, 5-diyl, and G is 2-(trans-1,4-cyclohexyl)ethyl.

One of the radicals L and E is preferably Cyc or Phe. E is preferably Cyc, Phe or Phe-Cyc. The media according to the invention preferably comprise one or more components selected from the compounds of the formulae (1), (2), (3), (4) and (5) in which L and E are selected from the group consisting of Cyc and Phe and simultaneously one or more components selected from the compounds of the formulae (1), (2), (3), (4) and (5) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (1), (2), (3), (4) and (5) in which the radicals L and E are selected from the group consisting of -Phe-Cyc-, -Cyc-Cyc-, -G-Phe- and -G-Cyc-.

In a smaller sub-group of the compounds of the formulae (1), (2), (3), (4) and (5), R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are referred to by the sub-formulae (1a), (2a), (3a), (4a) and (5a). In most of these compounds, R' and R" are different from one another, one of these radicals usually being alkyl, alkenyl, alkoxy or alkoxyalkyl.

In another smaller sub-group of the compounds of the formulae (1), (2), (3), (4) and (5), which is referred to as group B, E is

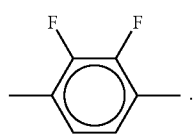

In the compounds of group B, which are referred to by the sub-formulae (1b), (2b), (3b), (4b) and (5b), R' and R" are as defined for the compounds of the sub-formulae (1a) to (5a) and are preferably alkyl, alkenyl, alkoxy or alkoxyalkyl.

In a further smaller sub-group of the compounds of the formulae (1), (2), (3), (4) and (5), R" is —CN; this sub-group is referred to below as group C, and the compounds of this sub-group are correspondingly described by sub-formulae (1c), (2c), (3c), (4c) and (5c). In the compounds of the sub-formulae (1c), (2c), (3c), (4c) and (5c), R' is as defined for the compounds of the sub-formulae (1a) to (5a) and is preferably alkyl, alkenyl, alkoxy or alkoxyalkyl.

Besides the preferred compounds of groups A, B and C, other compounds of the formulae (1), (2), (3), (4) and (5) having other variants of the proposed substituents are also customary. All these substances are obtainable by methods which are known from the literature or analogously thereto.

Besides the compounds of the general formulae (I), (II), (III), (IV), (V), (VI), (VII), (VIII), (IX), (X) and/or (XI) according to the invention, the media according to the invention preferably comprise one or more compounds from groups A, B and/or C. The proportions by weight of the compounds from these groups in the media according to the invention are:

group A: from 0 to 90%, preferably from 20 to 90%, in particular from 30 to 90%
group B: from 0 to 80%, preferably from 10 to 80%, in particular from 10 to 70%
group C: from 0 to 80%, preferably from 5 to 80%, in particular from 5 to 50%.

The media according to the invention preferably comprise from 1 to 40%, particularly preferably from 5 to 30%, of the compounds of the formulae (I), (II), (III), (IV), (V), (VI), (VII), (VIII), (IX), (X) and/or (XI) according to the invention. Preference is furthermore given to media comprising more than 40%, in particular from 45 to 90%, of compounds of the formulae (I), (II), (III), (IV), (V), (VI), (VII), (VII), (IX), (X) and/or (XI) according to the invention. The media preferably comprise three, four or five compounds of the formulae (I), (II), (III), (IV), (V), (VI), (VII), (VIII), (IX), (X) and/or (XI) according to the invention.

Examples of the compounds of the formulae (1), (2), (3), (4) and (5) are the compounds listed below:

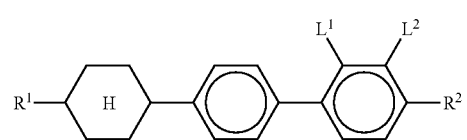

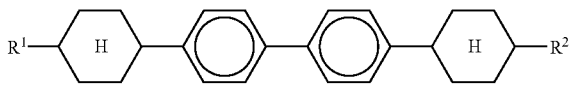

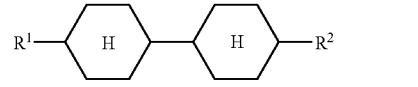

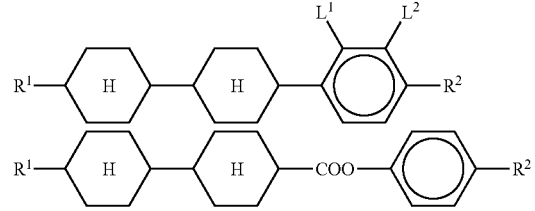

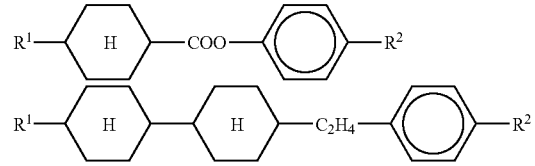

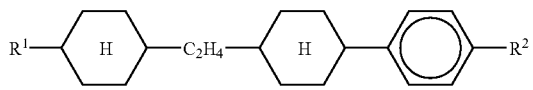

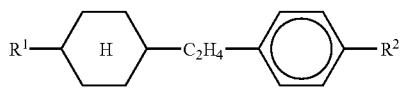

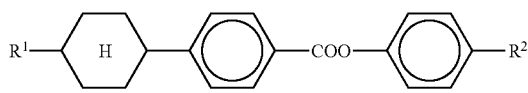

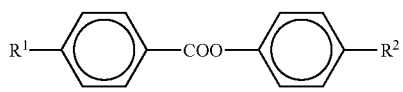

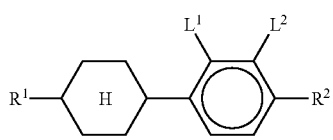

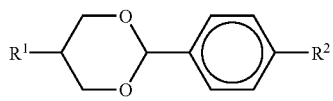

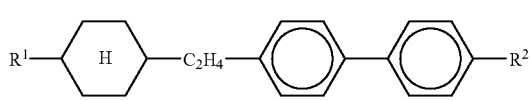

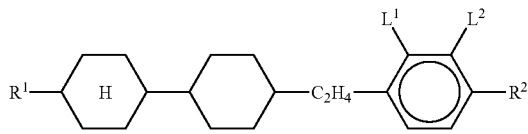

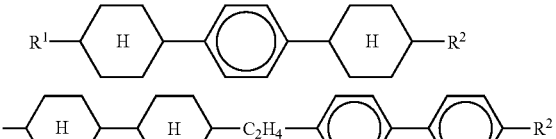

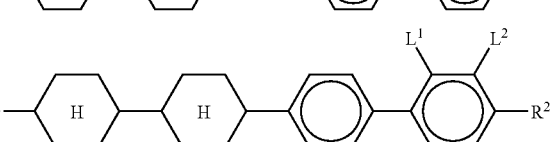

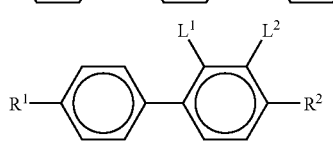

where $R^1$, $R^2$, independently of one another, $-C_nH_{2n+1}$ or $-OC_nH_{2n+1}$, and n=1 to 8, and $L^1$, $L^2$, independently of one another, —H or —F.

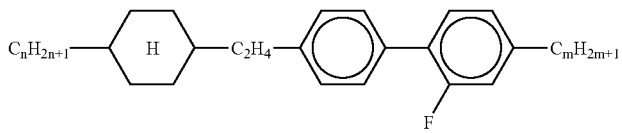

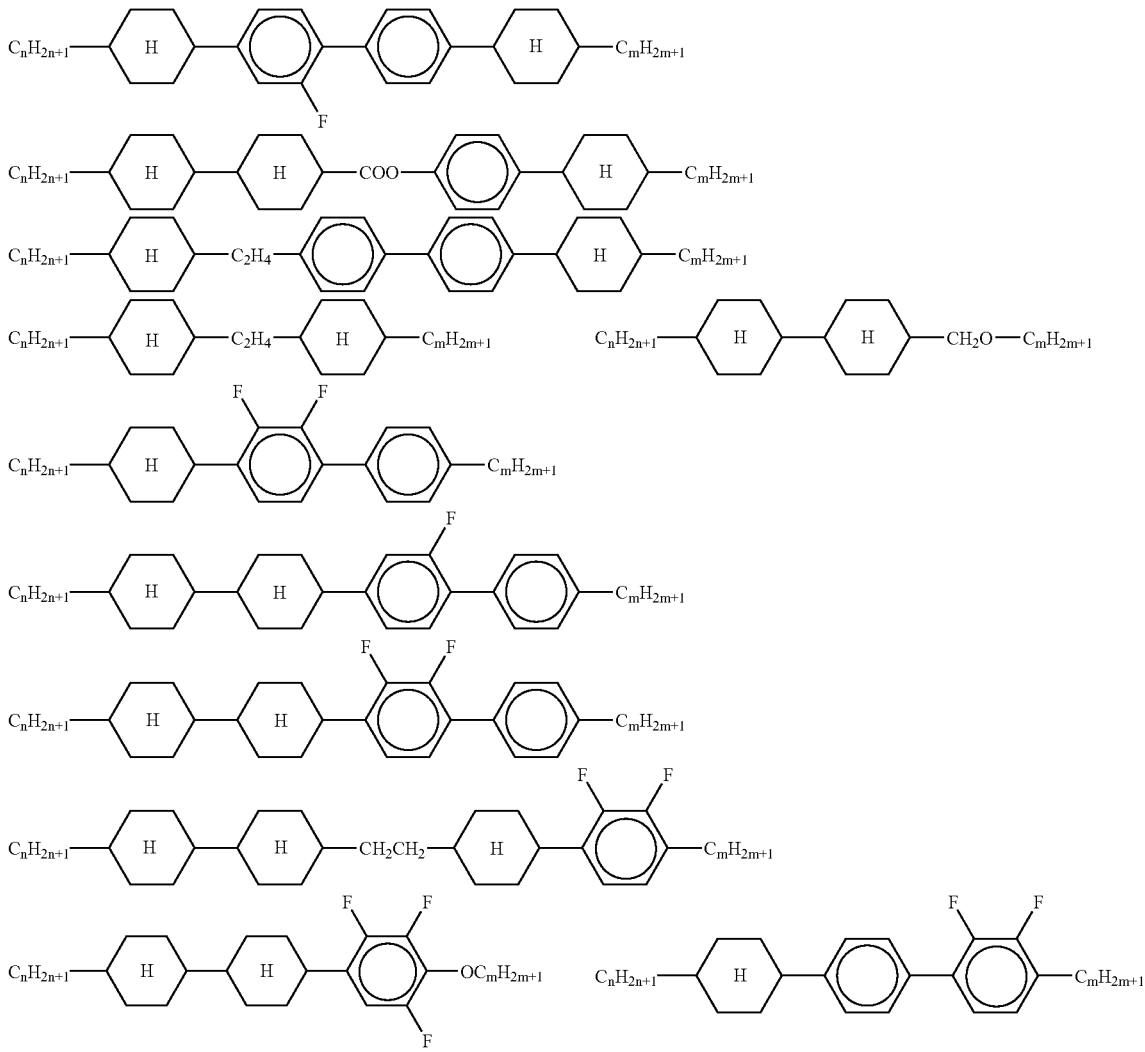

where m, n, independently of one another, from 1 to 8.

The media according to the invention are prepared in a manner conventional per se. In general, the components are dissolved in one another, advantageously at elevated temperature. By means of suitable additives, the liquid-crystalline phases of the present invention can be modified in such a way that they can be used in all types of liquid-crystal display elements that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the preparation of coloured guest-host systems or substances can be added in order to modify the dielectric anisotropy, the viscosity and/or the orientation of the nematic phases.

Owing to their negative $\Delta\epsilon$, the compounds of the formulae (II) to (VI) are particularly suitable for use in VA-TFT displays.

The present invention therefore also relates to electro-optical liquid-crystal display elements containing a liquid-crystalline medium according to the invention.

Owing to their high positive $\Delta\epsilon$, the compounds of the formulae (VII) to (XI) are particularly suitable for use in mesogenic control media, these control media being employed, in particular, in electro-optical light-control elements which are operated at a temperature at which the mesogenic control medium in the unaddressed state is in the isotropic phase.

The present invention therefore also relates to electro-optical light-control elements, as disclosed, for example, in DE 102 17 273 A1, which contain an electrode arrangement, at least one element for polarisation of the light and a mesogenic control medium, where the light-control element is operated at a temperature at which the mesogenic control medium in the unaddressed state is in the isotropic phase, and which are characterised in that the mesogenic control medium comprises one or more compounds of the formulae (VII) to (XI).

The invention is explained in greater detail below with reference to working examples, but without being restricted thereby.

EXAMPLES

The starting substances can be obtained by generally accessible literature procedures or commercially. The reactions described are known from the literature.

A) Preparation of the Naphthalene Derivatives

Example 1

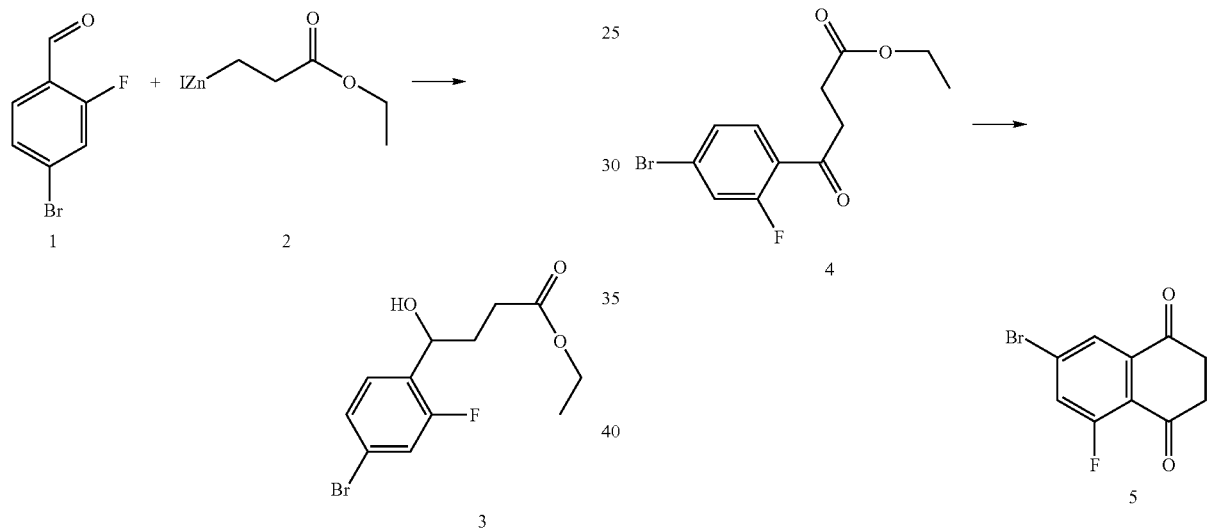

200 ml (100 mmol) of a 0.5 M solution of the zinc compound 2 in THF are added at −75° C. to a solution of 20.0 g (98.5 mmol) of the aldehyde 1 in 100 ml of THF. After 30 minutes, the cooling is removed. Water is added to the thawed batch, which is acidified using 1 N HCl solution and extracted with tert-butyl methyl (MTB) ether. Drying, evaporation and chromatography on silica gel gives the hydroxy ester 3.

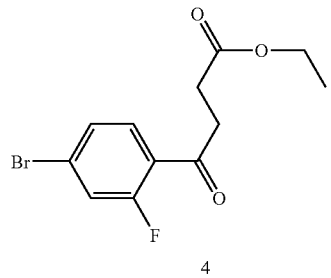

A solution of 10.0 g (32.7 mmol) of the hydroxy ester 3 is added at room temperature to a suspension of 40.0 mmol of pyridinium chlorochromate (PCC) on 50 g of Celite® in 150 ml of dichloromethane. When the reaction is complete (TLC), the batch is filtered, and the filter cake is washed with methylene chloride. Evaporation and chromatography on silica gel gives the keto ester 4.

9.0 g (29.7 mmol) of the keto ester 4 are added at 60° C. to 100 g of poly-phosphoric acid. The temperature is subsequently increased to 120° C. for 4 hours. After cooling, the batch is added to ice and extracted with tertbutyl methyl (MTB) ether. Drying, evaporation and crystallisation gives the diketone 5.

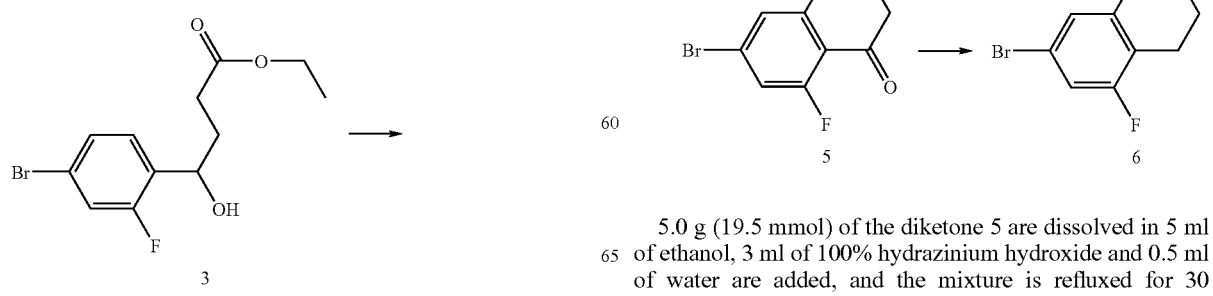

5.0 g (19.5 mmol) of the diketone 5 are dissolved in 5 ml of ethanol, 3 ml of 100% hydrazinium hydroxide and 0.5 ml of water are added, and the mixture is refluxed for 30 minutes. A solution of 800 mg of sodium in 15 ml of ethanol is subsequently added to the reaction vessel. The batch is heated at 140° C. until the evolution of nitrogen is complete. ⅔ of the ethanol is subsequently distilled off. The residue is diluted with 50 ml of water and extracted with ether. The extract is washed with 10% KOH, 5% HCl and 30% sodium hydrogensulfite solution. Drying, evaporation and chromatography on silica gel gives the tetrahydronaphthalene 6.

Example 2

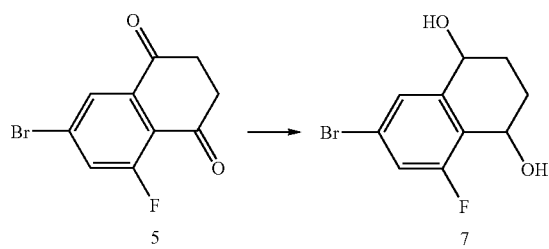

8.0 g (31.1 mmol) of the diketone 5 are dissolved in 150 ml of ethanol, and 2.4 g (65.0 mmol) of sodium borohydride are added in portions. When the reaction is complete (TLC), the batch is hydrolysed using water, the ethanol is removed under reduced pressure, and the residue is taken up in water and extracted with toluene. After evaporation, the product is employed in the next step without further purification.

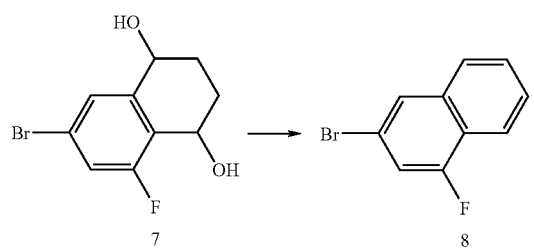

10.0 g (38.3 mmol) of the diol 7 are dissolved in 200 ml of toluene, 1 g of p-toluenesulfonic acid is added, and the mixture is refluxed until the separation of water is complete. Evaporation and filtration through silica gel gives the naphthalene derivative 8.

Example 3

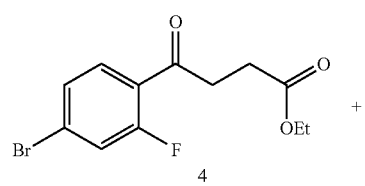

-continued

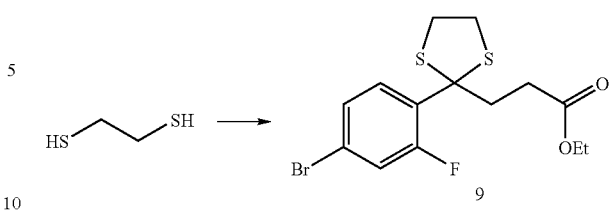

30 ml of boron trifluoride/diethyl ether complex are added under nitrogen to a solution of 15.0 g (49.5 mmol) of the keto ester 4 and 8.4 ml (100 mmol) of the dithiol in 150 ml of dichloromethane, and the mixture is stirred overnight. The batch is slowly added to saturated sodium hydrogencarbonate solution and deacidified. Drying, evaporation and chromatography on silica gel gives the protected ketone 9.

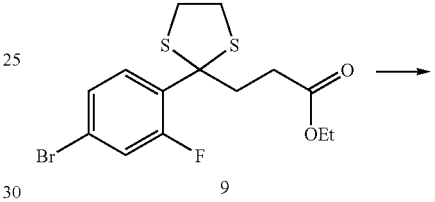

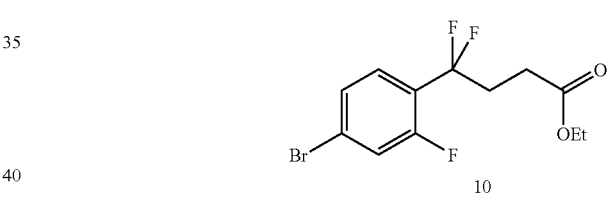

A solution of 10 g (26.4 mmol) of the protected ketone 9 in 60 ml of dichloromethane is added at −75° C. to a suspension of 30.2 g (105.2 mmol) of 1,3-dibromo-5,5-dimethylhydantoin in 60 ml of dichloromethane and 120 ml of a 65% solution of hydrogen fluoride in pyridine. The batch is slowly warmed to 0° C. over the course of 3 hours and added to 1500 ml of ice-cooled 2 N sodium hydroxide solution to which 120 ml of a 39% sodium hydrogensulfite solution have been added. The pH is adjusted to 8, and the aqueous phase is extracted with methylene chloride. Drying, evaporation and chromatography on silica gel gives the fluorinated ester 10.

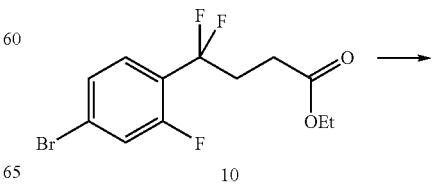

-continued

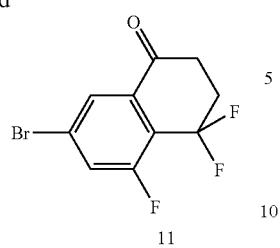

Ring closure of the fluorinated ester 10 to give compound 11 is carried out as described in Example 1.

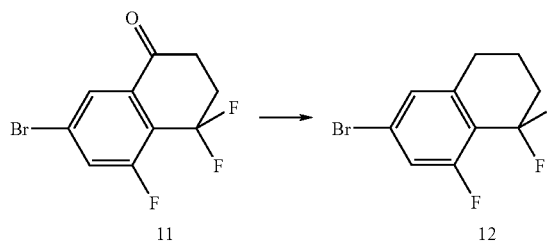

Reduction to the alkane 12 is carried out as described in Example 1.

Example 4

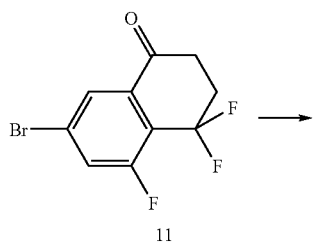

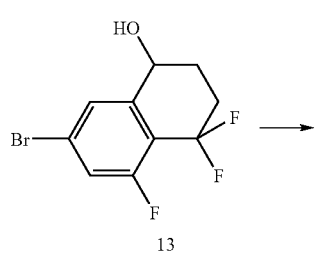

Reduction of compound 11 to the alcohol 13 and subsequent elimination of water to give the dihydronaphthalene derivative 14 are carried out as described in Example 2.

Example 5

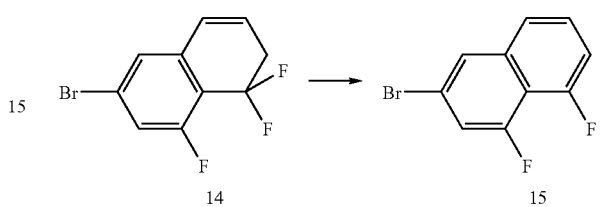

A solution of 9 g (34.2 mmol) of the dihydronaphthalene derivative 14 in 50 ml of THF is slowly added to a suspension of 4.5 g (40.1 mmol) of potassium tert-butoxide in 50 ml of THF, and the mixture is subsequently refluxed overnight. The cooled batch is diluted with water and extracted with diethyl ether. Drying, evaporation and chromatography on silica gel gives the naphthalene 15.

Example 6

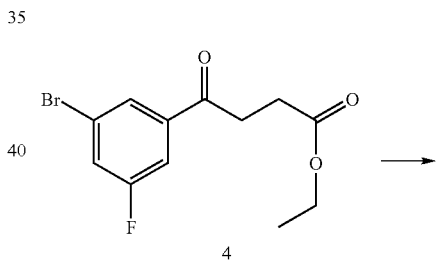

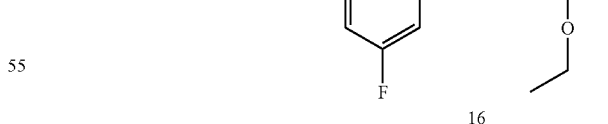

22 ml of a 2 M lithium diisopropylamide (LDA) solution are added at −78° C. to a solution of 6.8 g (21.4 mmol) of the keto ester 4 in 80 ml of THF. After 1 hour, 2.6 g (24.0 mmol) of chlorotrimethylsilane are added. After thawing, the solvents are removed under reduced pressure, and the residue is employed in the subsequent step without further purification.

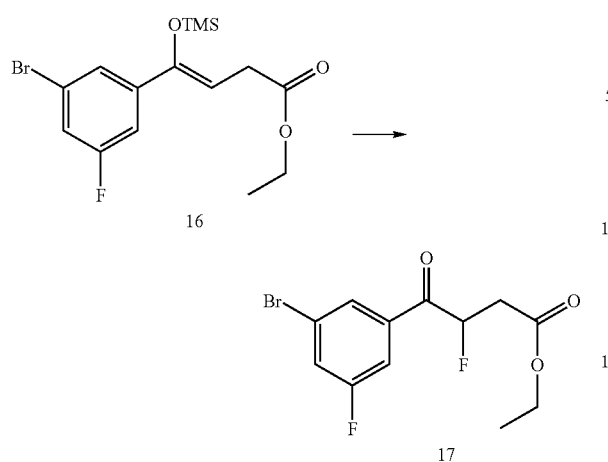

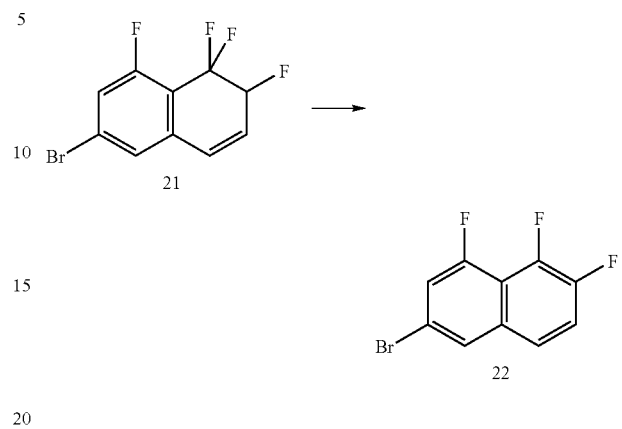

Example 7

4.9 g (19.8 mmol) of N-fluoropyridinium triflate are added to a solution of 5 g of the crude enol ether 16, and the mixture is refluxed overnight. The solvent is removed under reduced pressure, and the residue is purified by chromatography on silica gel, giving the fluorinated product 17.

The conversion of the dihydronaphthalene derivative 21 into the naphthalene derivative 22 is carried out as already described in Example 5.

Example 8

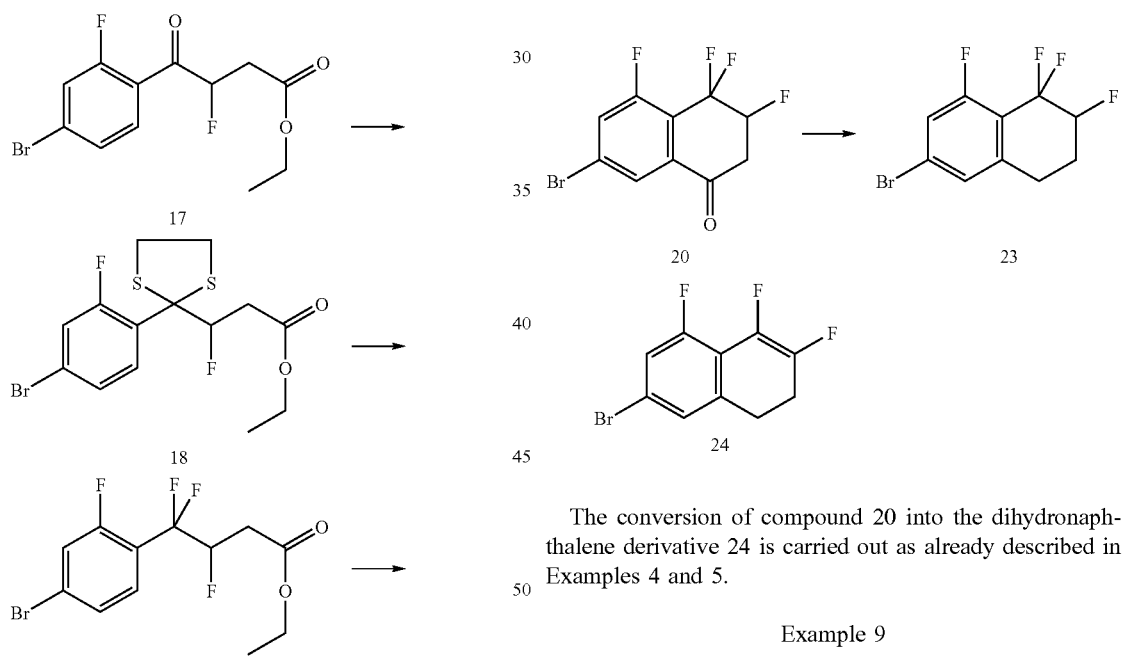

The conversion of compound 20 into the dihydronaphthalene derivative 24 is carried out as already described in Examples 4 and 5.

Example 9

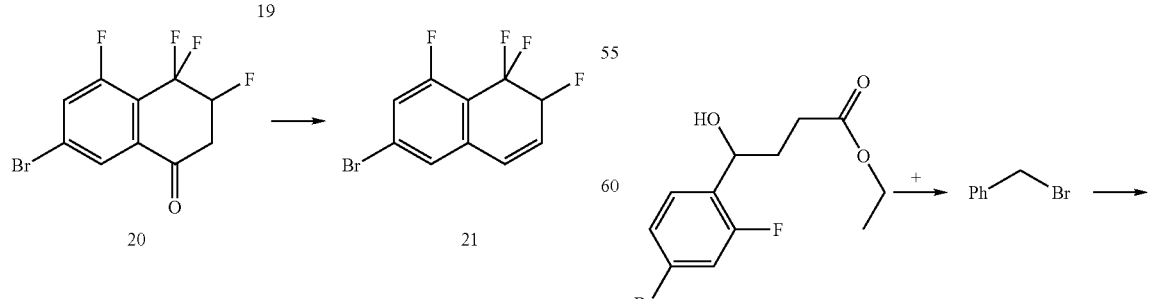

The conversions of the fluorinated product 17 into the dihydronaphthalene derivative 21 are carried out as already described in Examples 3 and 4.

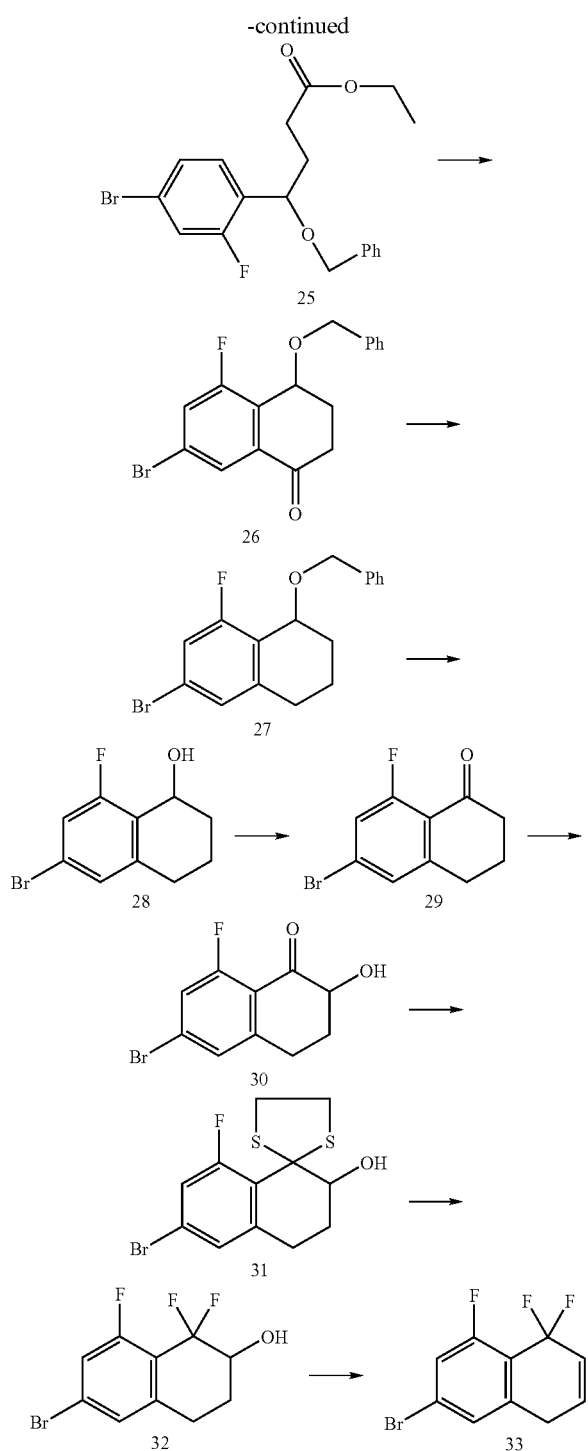

The ether 27 dissolved in THF is reacted on palladium/carbon catalyst in a hydrogen atmosphere. Evaporation and chromatography on silica gel gives the hydroxyl compound 28.

The conversion of the hydroxyl compound 28 into the ketone 29 is carried out as described in Example 1.

The ketone 29 is reacted with iodobenzene diacetate and KOH in methanol for four hours at from 0 to 20° C., giving the hydroxy ketone 30.

The conversion of the hydroxy ketone 30 into the dithiolane 31 and the conversion thereof into the fluorinated hydroxyl compound 32 take place as described in Example 3.

The fluorinated hydroxyl compound 32 is mixed with pyridine and POCl₃ with ice cooling. Alcohol is subsequently added. The reaction is carried out for four hours at 60° C. After cooling, the batch is added to ice-water and extracted with tert-butyl methyl (MTB) ether. Drying, evaporation and crystallisation gives the unsaturated fluorinated compound 33.

Example 10

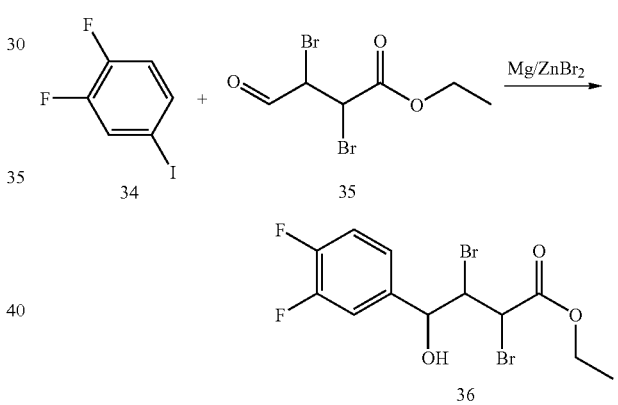

48.0 g (200 mmol) of the aromatic compound 34, 4.8 g (200 mmol) of magnesium and 200 ml of toluene/THF (4:1) are used to prepare the corresponding Grignard compound. 22.5 g (100 mmol) of zinc bromide are subsequently introduced. After 1 hour, 57.6 g (200 mmol) of the aldehyde 35 in 50 ml of solvent are added. After a further 2 hours, water is added to the batch, and the latter is acidified with dil. HCl solution. The aqueous phase is extracted three times with MTB ether. Drying, evaporation and chromatography gives 60.4 g of the ester 36.

The hydroxy ester 3 is reacted with benzyl bromide in dimethylformamide (DMF) in the presence of potassium carbonate for four hours at 120° C. After cooling, the batch is added to ice-water and extracted with tert-butyl methyl (MTB) ether. Drying, evaporation and crystallisation gives the ester 25.

The conversion of the ester 25 into the ketone 26 and the reduction thereof to the ether 27 takes place as described in Example 1.

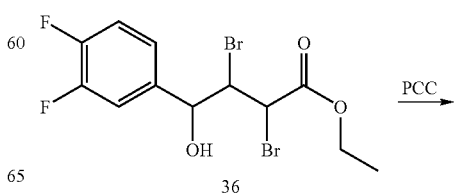

-continued

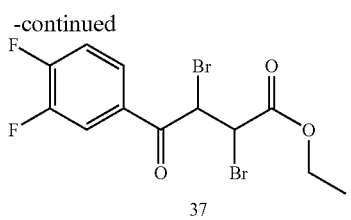
37

A solution of 50 g (124 mmol) of the ester 36 in 100 ml of dichloromethane is added at room temperature to a suspension of 40.0 g (186 mmol) of pyridinium chlorochromate (PCC) and 80 g of Celite in 300 ml of dichloromethane, and the mixture is stirred until conversion is complete (TLC). Filtration, evaporation and chromatography gives 47.1 g of the oxo ester 37.

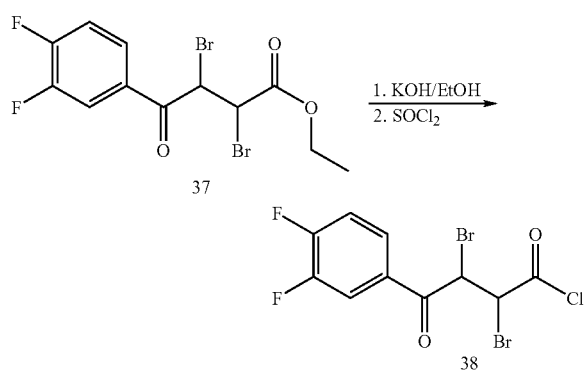

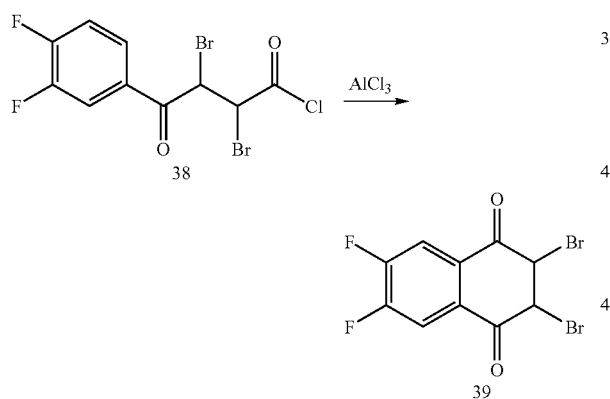

45 g (113 mol) of the ester 37 are refluxed for 20 hours with a solution of 20 g of potassium hydroxide in 50 ml of water and 150 ml of ethanol. The alcohol is subsequently removed, and the residue is taken up with water and acidified using HCl solution. The aqueous phase is extracted three times with MTB ether. The organic phase is dried and evaporated. 20 ml of thionyl chloride are added to the residue, and the mixture is refluxed until the evolution of gas is complete. Excess thionyl chloride is distilled off, and the residue is employed in the next step without further purification.

A solution of the acid chloride 38 in 50 ml of dichloromethane is added at −25° C. to a suspension of 18.0 g (136 mmol) of aluminium chloride in 50 ml of dichloromethane. The batch is held at a temperature below −12° C. until conversion is complete (TLC). The reaction is subsequently terminated by careful addition of water (50 ml). The precipitated solid is dissolved by means of HCl solution. The aqueous phase is extracted twice with dichloromethane, and the organic phase is dried and evaporated. Chromatography gives 30.2 g of the diketone 39.

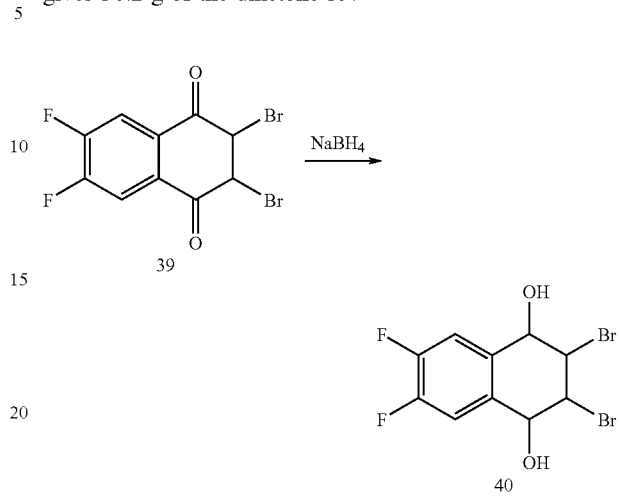

30.0 g (84.8 mmol) of the diketone 39 are dissolved in 150 ml of ethanol, and 6.3 g (170 mmol) of sodium borohydride are added in portions. When the reaction is complete (TLC), the batch is hydrolysed using water, the ethanol is removed under reduced pressure, and the residue is taken up in water and extracted with toluene. After evaporation, the product is employed in the next step without further purification.

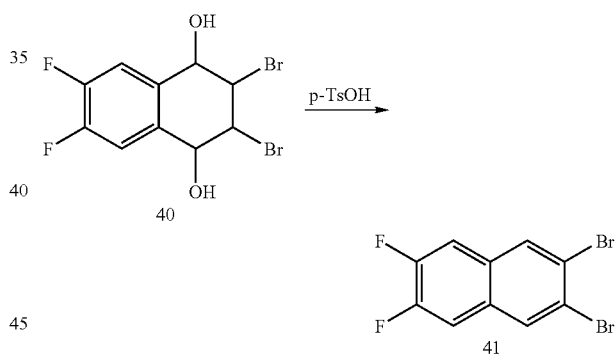

The crude diol 40 is dissolved in 200 ml of toluene, 2 g of p-toluenesulfonic acid are added, and the mixture is refluxed until the separation of water is complete. Evaporation and filtration through silica gel gives 24.7 g of the naphthalene 41.

B) Preparation of the Cyclopenta[b]Naphthalene Derivatives

Example 11

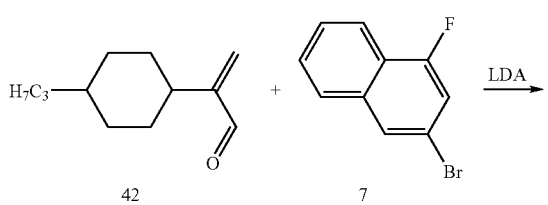

-continued

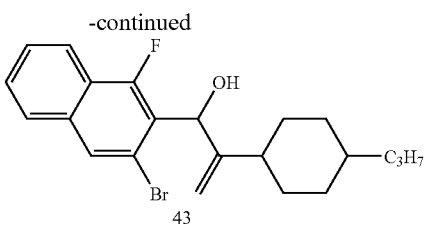
43

A solution of 13.5 g (60.0 mmol) of the bromofluoronaphthalene 7 in 10 ml of THF is added at −75° C. to 27.0 ml of a solution, diluted with 100 ml of THF, of 2 N lithium diisopropylamide (LDA) in cyclohexane/ethylbenzene/THF (52.4 mmol). After 2 hours at the low temperature, 8.5 g (47.3 mmol) of the aldehyde 42 in 10 ml of THF are added. After 30 minutes, the cooling is removed, and 100 ml of 1 N HCl are added to the batch at 20° C. Extraction of the aqueous phase, drying of the organic phase, evaporation and chromatography gives the allyl alcohol 43.

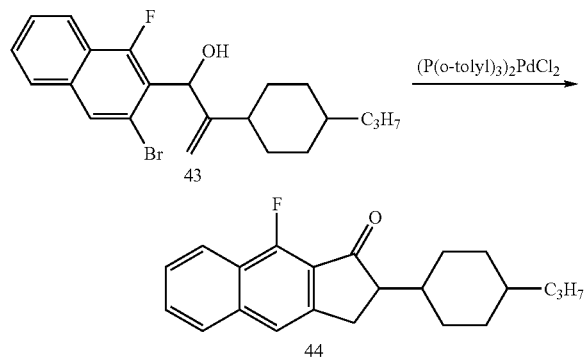

35.0 g (86.6 mmol) of the allyl alcohol 43, 5.5 g of bis(tri-o-tolylphosphine)-palladium dichloride and 50 ml of triethylamine are dissolved in 390 ml of acetonitrile, and the mixture is warmed at 90° C. until the allyl alcohol has reacted completely. The cooled batch is added to water. Extraction, drying, evaporation and chromatography gives the ketone 44.

Example 12

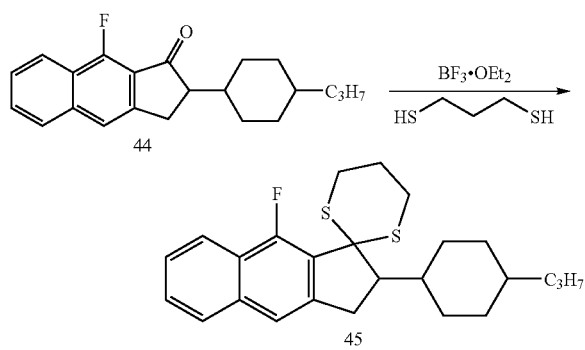

10.0 g (30.8 mmol) of the ketone 44 and 3.2 ml (31.0 mmol) of propanedithiol are dissolved in 50 ml of dichloromethane, and 7.0 ml of boron trifluoride/diethyl ether complex are added at from 6 to 7° C., and the mixture is subsequently stirred overnight at room temperature. The batch is added to 10 ml of saturated sodium hydrogencarbonate solution and stirred until the evolution of gas is complete. After extraction of the aqueous phase, drying of the organic phase, evaporation and filtration through silica gel, the resultant residue is employed in the next step without further purification.

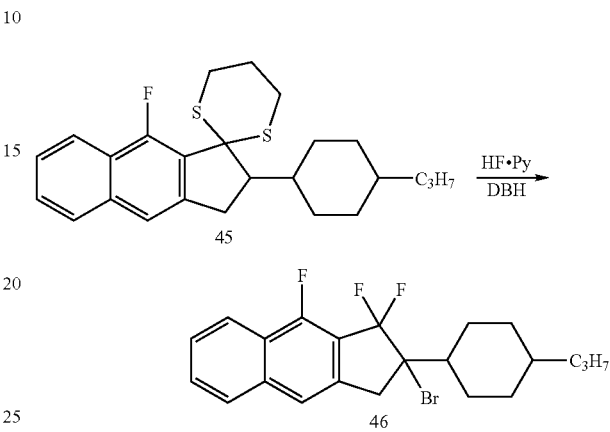

10.0 g of the crude thioketal 45 dissolved in 30 ml of dichloromethane are slowly added at −75° C. to a mixture of 28.6 g (100 mmol) of 1,3-dibromo-5,5-dimethylhydantoin (DBH), 80 ml of a 65% solution of hydrogen fluoride in pyridine and 50 ml of dichloromethane. The batch is subsequently stirred overnight at room temperature. The reaction mixture is added to ice-cooled hydrogen sulfite solution and deacidified using saturated sodium hydrogencarbonate solution and sodium hydroxide solution. Extraction, drying, evaporation, re-washing with water, chromatography and crystallisation from hexane gives the cyclopenta[b]naphthalene derivative 46.

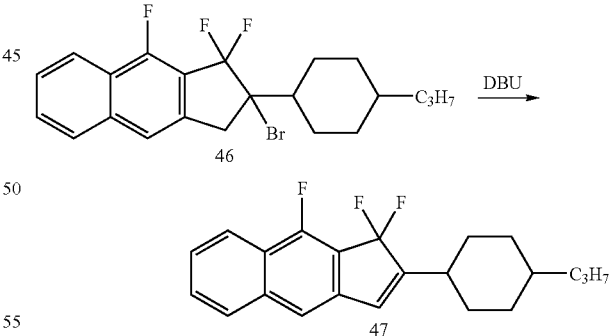

6.0 g (14.1 mmol) of the cyclopenta[b]naphthalene derivative 46 are dissolved in 50 ml of dichloromethane, 2.4 ml (16.0 mmol) of 1,8-diazabicyclo[5.4.0]undec-7-ene (DBU) are added, and the mixture is stirred at room temperature until the starting material has reacted completely. The batch is washed with water and saturated sodium chloride solution, evaporated and subjected to chromatography. The cyclopenta[b]naphthalene derivative 47 is isolated.

Example 13

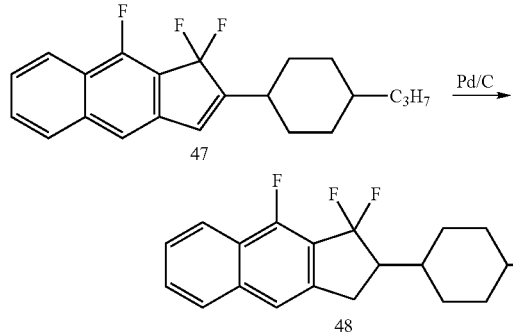

4.0 g (11.6 mmol) of the cyclopenta[b]naphthalene derivative 47 are dissolved in 50 ml of THF and hydrogenated at room temperature and atmospheric pressure on a palladium catalyst. Evaporation, chromatography on silica gel and crystallisation gives the cyclopenta[b]naphthalene derivative 48.

The Δn and Δε values of the compound according to the invention were obtained by extrapolation from liquid-crystalline mixtures consisting of 5% of the compound according to the invention and 95% of one of the two commercially available liquid-crystal mixtures ZLI 4792 and ZLI 2857 (Merck, Darmstadt).

Δn: 0.1418 (ZLI 4792, 589 nm, 20° C.)
ΔεF: 4.9 (ZLI 2857, 1 kHz, 20° C.)
Clearing point: 158.6° C. (ZLI 4792)

Example 14

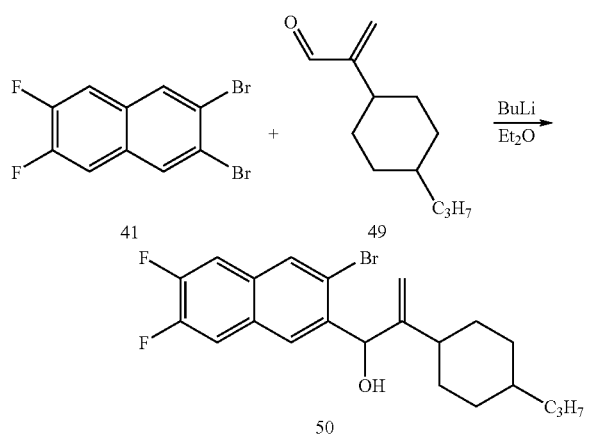

38.0 ml of an n-butyllithium solution in n-hexane are added at −75° C. to a solution of 20.0 g (62.1 mmol) of the naphthalene 41 in 100 ml of diethyl ether, and the mixture is stirred for 1 hour. 11.2 g (62.1 mmol) of the aldehyde 49 in 50 ml of diethyl ether are subsequently added, and the mixture is stirred overnight. Water is added to the batch. The aqueous phase is extracted with diethyl ether, and the organic phase is dried and evaporated. Chromatography gives 21.2 g of the allyl alcohol 50.

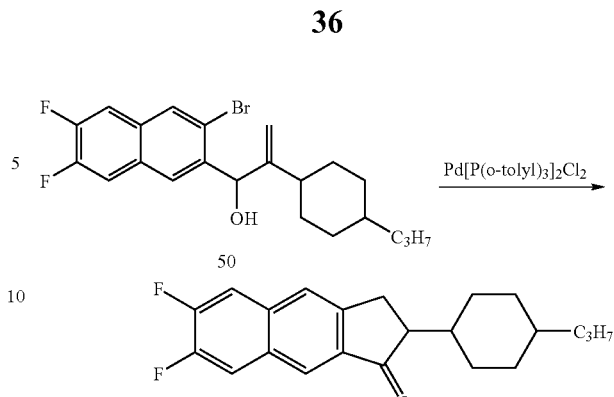

20.0 g (47.2 mmol) of the allyl alcohol 50 are dissolved in 175 ml of acetonitrile and 25 ml of triethylamine, 2.5 g of bis-tri-o-tolylphosphinepalladium(II) chloride are added, and the mixture is warmed at 90° C. until the starting material has disappeared (HPLC). The batch is subsequently added to saturated sodium chloride solution. Extraction with MTB ether, drying, evaporation and chromatography on silica gel gives 10.5 g of the ketone 51.

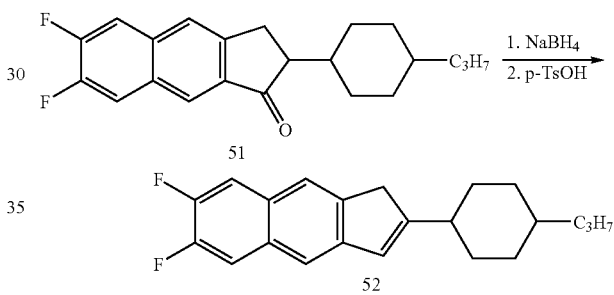

10.0 g (29.2 mmol) of the ketone 51 are dissolved in 75 ml of ethanol, and 3.2 g (86 mmol) of sodium borohydride are added in portions. When the reaction is complete (TLC), the batch is hydrolysed using water, the ethanol is removed under reduced pressure, and the residue is taken up in water and extracted with toluene. After evaporation, the product is employed in the next step without further purification. The crude alcohol is dissolved in 100 ml of toluene, 1 g of p-toluenesulfonic acid is added, and the mixture is refluxed until the separation of water is complete. Evaporation and filtration through silica gel gives 8.5 of the naphthalene 52.

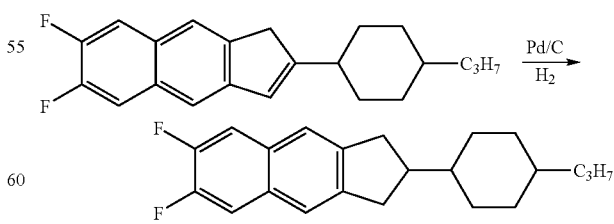

8.0 g (25.5 mmol) of the naphthalene 52 are dissolved in 50 ml of THF and hydrogenated on a palladium catalyst. Evaporation and chromatography on silica gel gives 7.9 g of the hydrogenated substance 53.

The following compounds are prepared analogously to Examples 1 to 14 or analogously to known synthetic steps:

Examples 15 to 29

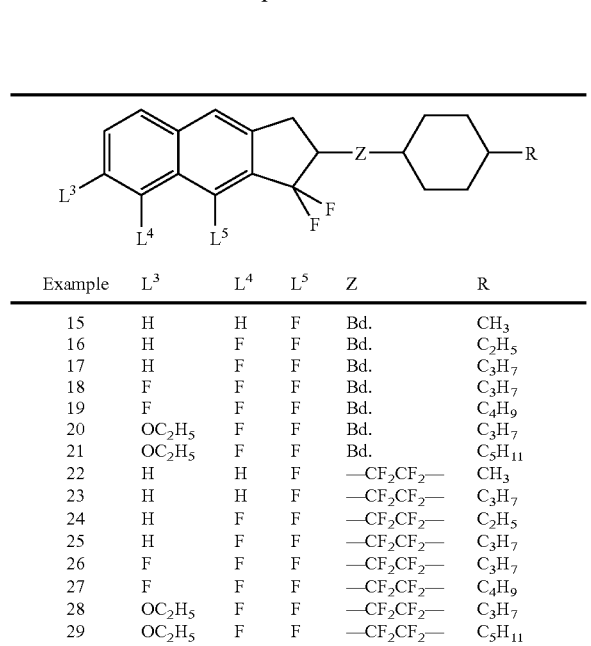

| Example | L³ | L⁴ | L⁵ | Z | R |
|---|---|---|---|---|---|
| 15 | H | H | F | Bd. | CH₃ |
| 16 | H | F | F | Bd. | C₂H₅ |
| 17 | H | F | F | Bd. | C₃H₇ |
| 18 | F | F | F | Bd. | C₃H₇ |
| 19 | F | F | F | Bd. | C₄H₉ |
| 20 | OC₂H₅ | F | F | Bd. | C₃H₇ |
| 21 | OC₂H₅ | F | F | Bd. | C₅H₁₁ |
| 22 | H | H | F | —CF₂CF₂— | CH₃ |
| 23 | H | H | F | —CF₂CF₂— | C₃H₇ |
| 24 | H | F | F | —CF₂CF₂— | C₂H₅ |
| 25 | H | F | F | —CF₂CF₂— | C₃H₇ |
| 26 | F | F | F | —CF₂CF₂— | C₃H₇ |
| 27 | F | F | F | —CF₂CF₂— | C₄H₉ |
| 28 | OC₂H₅ | F | F | —CF₂CF₂— | C₃H₇ |
| 29 | OC₂H₅ | F | F | —CF₂CF₂— | C₅H₁₁ |

Bd. = single bond

Examples 30 to 53

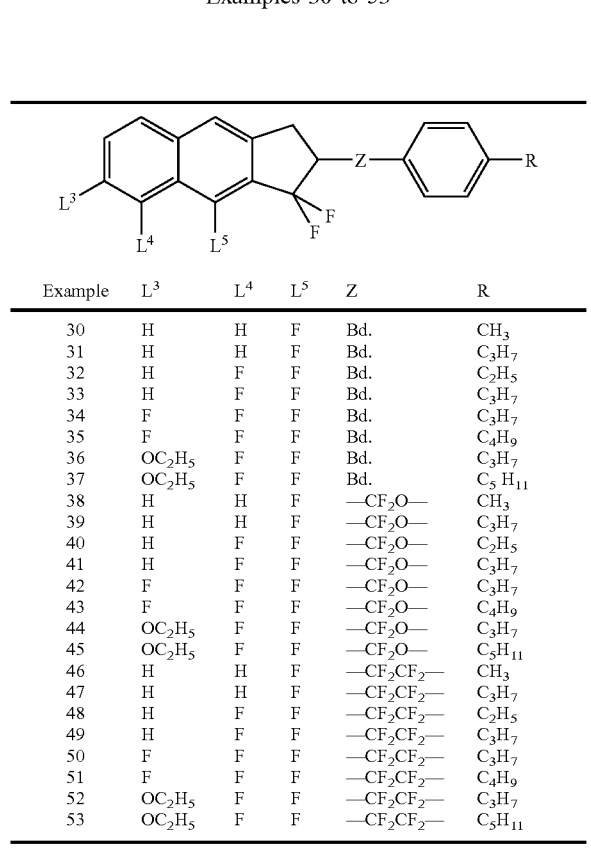

| Example | L³ | L⁴ | L⁵ | Z | R |
|---|---|---|---|---|---|
| 30 | H | H | F | Bd. | CH₃ |
| 31 | H | H | F | Bd. | C₃H₇ |
| 32 | H | F | F | Bd. | C₂H₅ |
| 33 | H | F | F | Bd. | C₃H₇ |
| 34 | F | F | F | Bd. | C₃H₇ |
| 35 | F | F | F | Bd. | C₄H₉ |
| 36 | OC₂H₅ | F | F | Bd. | C₃H₇ |
| 37 | OC₂H₅ | F | F | Bd. | C₅H₁₁ |
| 38 | H | H | F | —CF₂O— | CH₃ |
| 39 | H | H | F | —CF₂O— | C₃H₇ |
| 40 | H | F | F | —CF₂O— | C₂H₅ |
| 41 | H | F | F | —CF₂O— | C₃H₇ |
| 42 | F | F | F | —CF₂O— | C₃H₇ |
| 43 | F | F | F | —CF₂O— | C₄H₉ |
| 44 | OC₂H₅ | F | F | —CF₂O— | C₃H₇ |
| 45 | OC₂H₅ | F | F | —CF₂O— | C₅H₁₁ |
| 46 | H | H | F | —CF₂CF₂— | CH₃ |
| 47 | H | H | F | —CF₂CF₂— | C₃H₇ |
| 48 | H | F | F | —CF₂CF₂— | C₂H₅ |
| 49 | H | F | F | —CF₂CF₂— | C₃H₇ |
| 50 | F | F | F | —CF₂CF₂— | C₃H₇ |
| 51 | F | F | F | —CF₂CF₂— | C₄H₉ |
| 52 | OC₂H₅ | F | F | —CF₂CF₂— | C₃H₇ |
| 53 | OC₂H₅ | F | F | —CF₂CF₂— | C₅H₁₁ |

Bd. = single bond

Examples 54 to 77

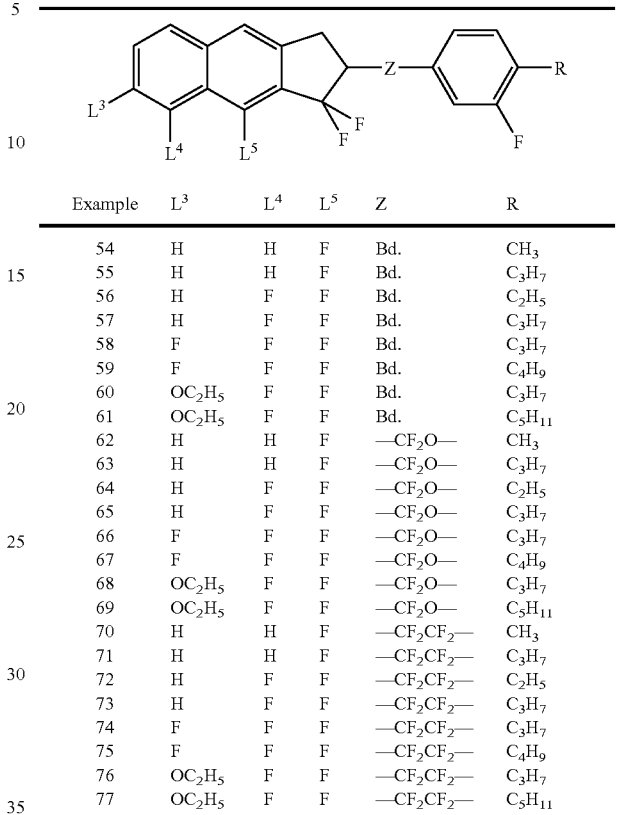

| Example | L³ | L⁴ | L⁵ | Z | R |
|---|---|---|---|---|---|
| 54 | H | H | F | Bd. | CH₃ |
| 55 | H | H | F | Bd. | C₃H₇ |
| 56 | H | F | F | Bd. | C₂H₅ |
| 57 | H | F | F | Bd. | C₃H₇ |
| 58 | F | F | F | Bd. | C₃H₇ |
| 59 | F | F | F | Bd. | C₄H₉ |
| 60 | OC₂H₅ | F | F | Bd. | C₃H₇ |
| 61 | OC₂H₅ | F | F | Bd. | C₅H₁₁ |
| 62 | H | H | F | —CF₂O— | CH₃ |
| 63 | H | H | F | —CF₂O— | C₃H₇ |
| 64 | H | F | F | —CF₂O— | C₂H₅ |
| 65 | H | F | F | —CF₂O— | C₃H₇ |
| 66 | F | F | F | —CF₂O— | C₃H₇ |
| 67 | F | F | F | —CF₂O— | C₄H₉ |
| 68 | OC₂H₅ | F | F | —CF₂O— | C₃H₇ |
| 69 | OC₂H₅ | F | F | —CF₂O— | C₅H₁₁ |
| 70 | H | H | F | —CF₂CF₂— | CH₃ |
| 71 | H | H | F | —CF₂CF₂— | C₃H₇ |
| 72 | H | F | F | —CF₂CF₂— | C₂H₅ |
| 73 | H | F | F | —CF₂CF₂— | C₃H₇ |
| 74 | F | F | F | —CF₂CF₂— | C₃H₇ |
| 75 | F | F | F | —CF₂CF₂— | C₄H₉ |
| 76 | OC₂H₅ | F | F | —CF₂CF₂— | C₃H₇ |
| 77 | OC₂H₅ | F | F | —CF₂CF₂— | C₅H₁₁ |

Bd. = single bond

Examples 78 to 93

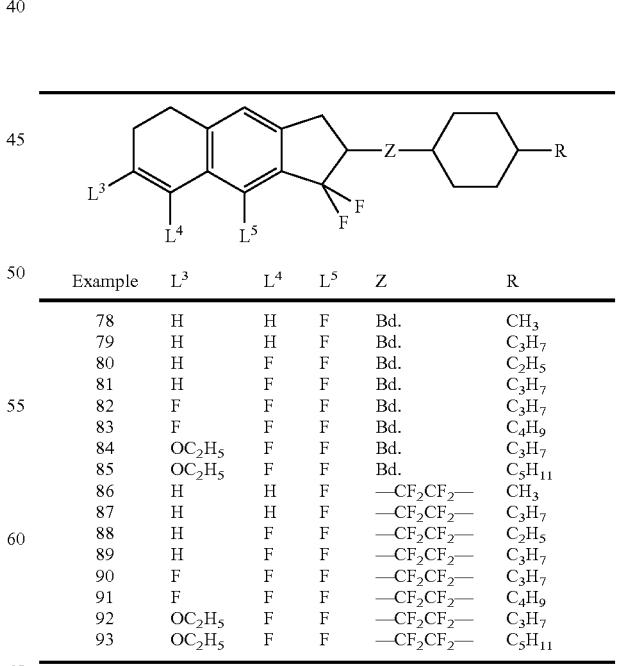

| Example | L³ | L⁴ | L⁵ | Z | R |
|---|---|---|---|---|---|
| 78 | H | H | F | Bd. | CH₃ |
| 79 | H | H | F | Bd. | C₃H₇ |
| 80 | H | F | F | Bd. | C₂H₅ |
| 81 | H | F | F | Bd. | C₃H₇ |
| 82 | F | F | F | Bd. | C₃H₇ |
| 83 | F | F | F | Bd. | C₄H₉ |
| 84 | OC₂H₅ | F | F | Bd. | C₃H₇ |
| 85 | OC₂H₅ | F | F | Bd. | C₅H₁₁ |
| 86 | H | H | F | —CF₂CF₂— | CH₃ |
| 87 | H | H | F | —CF₂CF₂— | C₃H₇ |
| 88 | H | F | F | —CF₂CF₂— | C₂H₅ |
| 89 | H | F | F | —CF₂CF₂— | C₃H₇ |
| 90 | F | F | F | —CF₂CF₂— | C₃H₇ |
| 91 | F | F | F | —CF₂CF₂— | C₄H₉ |
| 92 | OC₂H₅ | F | F | —CF₂CF₂— | C₃H₇ |
| 93 | OC₂H₅ | F | F | —CF₂CF₂— | C₅H₁₁ |

Bd. = single bond

Examples 94 to 117

[Structure: bicyclic system with L³, L⁴, L⁵ substituents, connected via Z to phenyl-R, with F substituent]

| Example | L³ | L⁴ | L⁵ | Z | R |
|---|---|---|---|---|---|
| 94 | H | H | F | Bd. | CH₃ |
| 95 | H | H | F | Bd. | C₃H₇ |
| 96 | H | F | F | Bd. | C₂H₅ |
| 97 | H | F | F | Bd. | C₃H₇ |
| 98 | F | F | F | Bd. | C₃H₇ |
| 99 | F | F | F | Bd. | C₄H₉ |
| 100 | OC₂H₅ | F | F | Bd. | C₃H₇ |
| 101 | OC₂H₅ | F | F | Bd. | C₅H₁₁ |
| 102 | H | H | F | —CF₂O— | CH₃ |
| 103 | H | H | F | —CF₂O— | C₃H₇ |
| 104 | H | F | F | —CF₂O— | C₂H₅ |
| 105 | H | F | F | —CF₂O— | C₃H₇ |
| 106 | F | F | F | —CF₂O— | C₃H₇ |
| 107 | F | F | F | —CF₂O— | C₄H₉ |
| 108 | OC₂H₅ | F | F | —CF₂O— | C₃H₇ |
| 109 | OC₂H₅ | F | F | —CF₂O— | C₅H₁₁ |
| 110 | H | H | F | —CF₂CF₂— | CH₃ |
| 111 | H | H | F | —CF₂CF₂— | C₃H₇ |
| 112 | H | F | F | —CF₂CF₂— | C₂H₅ |
| 113 | H | F | F | —CF₂CF₂— | C₃H₇ |
| 114 | F | F | F | —CF₂CF₂— | C₃H₇ |
| 115 | F | F | F | —CF₂CF₂— | C₄H₉ |
| 116 | OC₂H₅ | F | F | —CF₂CF₂— | C₃H₇ |
| 117 | OC₂H₅ | F | F | —CF₂CF₂— | C₅H₁₁ |

Bd. = single bond

Examples 118 to 141

[Structure: bicyclic system with L³, L⁴, L⁵ substituents, connected via Z to difluorophenyl-R]

| Example | L³ | L⁴ | L⁵ | Z | R |
|---|---|---|---|---|---|
| 118 | H | H | F | Bd. | CH₃ |
| 119 | H | H | F | Bd. | C₃H₇ |
| 120 | H | F | F | Bd. | C₂H₅ |
| 121 | H | F | F | Bd. | C₃H₇ |
| 122 | F | F | F | Bd. | C₃H₇ |
| 123 | F | F | F | Bd. | C₄H₉ |
| 124 | OC₂H₅ | F | F | Bd. | C₃H₇ |
| 125 | OC₂H₅ | F | F | Bd. | C₅H₁₁ |
| 126 | H | H | F | —CF₂O— | CH₃ |
| 127 | H | H | F | —CF₂O— | C₃H₇ |
| 128 | H | F | F | —CF₂O— | C₂H₅ |
| 129 | H | F | F | —CF₂O— | C₃H₇ |
| 130 | F | F | F | —CF₂O— | C₃H₇ |
| 131 | F | F | F | —CF₂O— | C₄H₉ |
| 132 | OC₂H₅ | F | F | —CF₂O— | C₃H₇ |
| 133 | OC₂H₅ | F | F | —CF₂O— | C₅H₁₁ |
| 134 | H | H | F | —CF₂CF₂— | CH₃ |
| 135 | H | H | F | —CF₂CF₂— | C₃H₇ |
| 136 | H | F | F | —CF₂CF₂— | C₂H₅ |
| 137 | H | F | F | —CF₂CF₂— | C₃H₇ |
| 138 | F | F | F | —CF₂CF₂— | C₃H₇ |
| 139 | F | F | F | —CF₂CF₂— | C₄H₉ |
| 140 | OC₂H₅ | F | F | —CF₂CF₂— | C₃H₇ |
| 141 | OC₂H₅ | F | F | —CF₂CF₂— | C₅H₁₁ |

Bd. = single bond

Examples 142 to 157

[Structure: bicyclic system with L³, L⁴, L⁵ substituents, connected via Z to cyclohexyl-R]

| Example | L³ | L⁴ | L⁵ | Z | R |
|---|---|---|---|---|---|
| 142 | H | H | H | Bd. | CH₃ |
| 143 | H | H | H | Bd. | C₃H₇ |
| 144 | H | F | F | Bd. | C₂H₅ |
| 145 | H | F | F | Bd. | C₃H₇ |
| 146 | F | F | F | Bd. | C₃H₇ |
| 147 | F | F | F | Bd. | C₄H₉ |
| 148 | OC₂H₅ | F | F | Bd. | C₃H₇ |
| 149 | OC₂H₅ | F | F | Bd. | C₅H₁₁ |
| 150 | H | H | H | —CF₂CF₂— | CH₃ |
| 151 | H | H | H | —CF₂CF₂— | C₃H₇ |
| 152 | H | F | F | —CF₂CF₂— | C₂H₅ |
| 153 | H | F | F | —CF₂CF₂— | C₃H₇ |
| 154 | F | F | F | —CF₂CF₂— | C₃H₇ |
| 155 | F | F | F | —CF₂CF₂— | C₄H₉ |
| 156 | OC₂H₅ | F | F | —CF₂CF₂— | C₃H₇ |
| 157 | OC₂H₅ | F | F | —CF₂CF₂— | C₅H₁₁ |

Bd. = single bond

Examples 158 to 181

[Structure: bicyclic system with L³, L⁴, L⁵ substituents and F, connected via Z to phenyl-R]

| Example | L³ | L⁴ | L⁵ | Z | R |
|---|---|---|---|---|---|
| 158 | H | H | H | Bd. | CH₃ |
| 159 | H | H | H | Bd. | C₃H₇ |
| 160 | H | F | F | Bd. | C₂H₅ |
| 161 | H | F | F | Bd. | C₃H₇ |
| 162 | F | F | F | Bd. | C₃H₇ |
| 163 | F | F | F | Bd. | C₄H₉ |
| 164 | OC₂H₅ | F | F | Bd. | C₃H₇ |
| 165 | OC₂H₅ | F | F | Bd. | C₅H₁₁ |
| 166 | H | H | H | —CF₂O— | CH₃ |
| 167 | H | H | H | —CF₂O— | C₃H₇ |
| 168 | H | F | F | —CF₂O— | C₂H₅ |

-continued

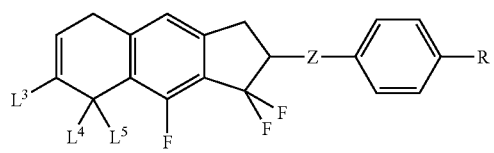

| Example | L³ | L⁴ | L⁵ | Z | R |
|---|---|---|---|---|---|
| 169 | H | F | F | —CF₂O— | C₃H₇ |
| 170 | F | F | F | —CF₂O— | C₃H₇ |
| 171 | F | F | F | —CF₂O— | C₄H₉ |
| 172 | OC₂H₅ | F | F | —CF₂O— | C₃H₇ |
| 173 | OC₂H₅ | F | F | —CF₂O— | C₅H₁₁ |
| 174 | H | H | H | —CF₂CF₂— | CH₃ |
| 175 | H | H | H | —CF₂CF₂— | C₃H₇ |
| 176 | H | F | F | —CF₂CF₂— | C₂H₅ |
| 177 | H | F | F | —CF₂CF₂— | C₃H₇ |
| 178 | F | F | F | —CF₂CF₂— | C₃H₇ |
| 179 | F | F | F | —CF₂CF₂— | C₄H₉ |
| 180 | OC₂H₅ | F | F | —CF₂CF₂— | C₃H₇ |
| 181 | OC₂H₅ | F | F | —CF₂CF₂— | C₅H₁₁ |

Bd. = single bond

Examples 182 to 205

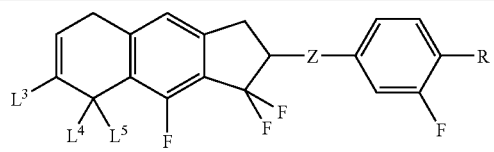

| Example | L³ | L⁴ | L⁵ | Z | R |
|---|---|---|---|---|---|
| 182 | H | H | H | Bd. | CH₃ |
| 183 | H | H | H | Bd. | C₃H₇ |
| 184 | H | F | F | Bd. | C₂H₅ |
| 185 | H | F | F | Bd. | C₃H₇ |
| 186 | F | F | F | Bd. | C₃H₇ |
| 187 | F | F | F | Bd. | C₄H₉ |
| 188 | OC₂H₅ | F | F | Bd. | C₃H₇ |
| 189 | OC₂H₅ | F | F | Bd. | C₅H₁₁ |
| 190 | H | H | H | —CF₂O— | CH₃ |
| 191 | H | H | H | —CF₂O— | C₃H₇ |
| 192 | H | F | F | —CF₂O— | C₂H₅ |
| 193 | H | F | F | —CF₂O— | C₃H₇ |
| 194 | F | F | F | —CF₂O— | C₃H₇ |
| 195 | F | F | F | —CF₂O— | C₄H₉ |
| 196 | OC₂H₅ | F | F | —CF₂O— | C₃H₇ |
| 197 | OC₂H₅ | F | F | —CF₂O— | C₅H₁₁ |
| 198 | H | H | H | —CF₂CF₂— | CH₃ |
| 199 | H | H | H | —CF₂CF₂— | C₃H₇ |
| 200 | H | F | F | —CF₂CF₂— | C₂H₅ |
| 201 | H | F | F | —CF₂CF₂— | C₃H₇ |
| 202 | F | F | F | —CF₂CF₂— | C₃H₇ |
| 203 | F | F | F | —CF₂CF₂— | C₄H₉ |
| 204 | OC₂H₅ | F | F | —CF₂CF₂— | C₃H₇ |
| 205 | OC₂H₅ | F | F | —CF₂CF₂— | C₅H₁₁ |

Bd. = single bond

Examples 206 to 217

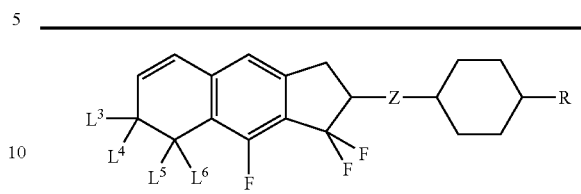

| Example | L³ | L⁴ | L⁵ | L⁶ | Z | R |
|---|---|---|---|---|---|---|
| 206 | H | H | H | H | Bd. | CH₃ |
| 207 | H | H | H | H | Bd. | C₃H₇ |
| 208 | H | H | F | F | Bd. | C₂H₅ |
| 209 | H | H | F | F | Bd. | C₃H₇ |
| 210 | F | F | F | F | Bd. | C₃H₇ |
| 211 | F | F | F | F | Bd. | C₄H₉ |
| 212 | H | H | H | H | —CF₂CF₂— | CH₃ |
| 213 | H | H | H | H | —CF₂CF₂— | C₃H₇ |
| 214 | H | H | F | F | —CF₂CF₂— | C₂H₅ |
| 215 | H | H | F | F | —CF₂CF₂— | C₃H₇ |
| 216 | F | F | F | F | —CF₂CF₂— | C₃H₇ |
| 217 | F | F | F | F | —CF₂CF₂— | C₄H₉ |

Bd. = single bond

Examples 218 to 235

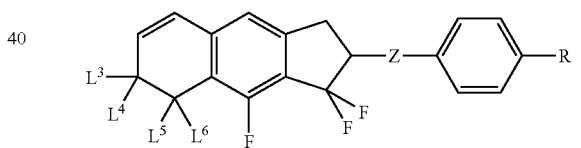

| Example | L³ | L⁴ | L⁵ | L⁶ | Z | R |
|---|---|---|---|---|---|---|
| 218 | H | H | H | H | Bd. | CH₃ |
| 219 | H | H | H | H | Bd. | C₃H₇ |
| 220 | H | H | F | F | Bd. | C₂H₅ |
| 221 | H | H | F | F | Bd. | C₃H₇ |
| 222 | F | F | F | F | Bd. | C₃H₇ |
| 223 | F | F | F | F | Bd. | C₄H₉ |
| 224 | H | H | H | H | —CF₂O— | CH₃ |
| 225 | H | H | H | H | —CF₂O— | C₃H₇ |
| 226 | H | H | F | F | —CF₂O— | C₂H₅ |
| 227 | H | H | F | F | —CF₂O— | C₃H₇ |
| 228 | F | F | F | F | —CF₂O— | C₃H₇ |
| 229 | F | F | F | F | —CF₂O— | C₄H₉ |
| 230 | H | H | H | H | —CF₂CF₂— | CH₃ |
| 231 | H | H | H | H | —CF₂CF₂— | C₃H₇ |
| 232 | H | H | F | F | —CF₂CF₂— | C₂H₅ |
| 233 | H | H | F | F | —CF₂CF₂— | C₃H₇ |
| 234 | F | F | F | F | —CF₂CF₂— | C₃H₇ |
| 235 | F | F | F | F | —CF₂CF₂— | C₄H₉ |

Bd. = single bond

Examples 236 to 253

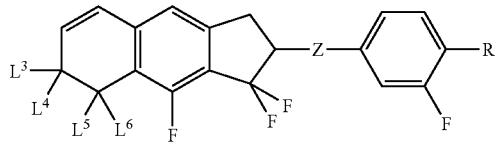

| Example | L³ | L⁴ | L⁵ | L⁶ | Z | R |
|---|---|---|---|---|---|---|
| 236 | H | H | H | H | Bd. | CH₃ |
| 237 | H | H | H | H | Bd. | C₃H₇ |
| 238 | H | H | F | F | Bd. | C₂H₅ |
| 239 | H | H | F | F | Bd. | C₃H₇ |
| 240 | F | F | F | F | Bd. | C₃H₇ |
| 241 | F | F | F | F | Bd. | C₄H₉ |
| 242 | H | H | H | H | —CF₂O— | CH₃ |
| 243 | H | H | H | H | —CF₂O— | C₃H₇ |
| 244 | H | H | F | F | —CF₂O— | C₂H₅ |
| 245 | H | H | F | F | —CF₂O— | C₃H₇ |
| 246 | F | F | F | F | —CF₂O— | C₃H₇ |
| 247 | F | F | F | F | —CF₂O— | C₄H₉ |
| 248 | H | H | H | H | —CF₂CF₂— | CH₃ |
| 249 | H | H | H | H | —CF₂CF₂— | C₃H₇ |
| 250 | H | H | F | F | —CF₂CF₂— | C₂H₅ |
| 251 | H | H | F | F | —CF₂CF₂— | C₃H₇ |
| 252 | F | F | F | F | —CF₂CF₂— | C₃H₇ |
| 253 | F | F | F | F | —CF₂CF₂— | C₄H₉ |

Bd. = single bond

Examples 254 to 265

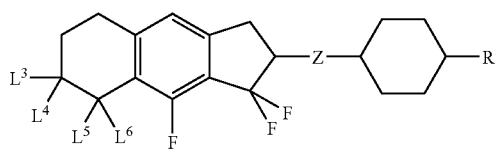

| Example | L³ | L⁴ | L⁵ | L⁶ | Z | R |
|---|---|---|---|---|---|---|
| 254 | H | H | H | H | Bd. | CH₃ |
| 255 | H | H | H | H | Bd. | C₃H₇ |
| 256 | H | H | F | F | Bd. | C₂H₅ |
| 257 | H | H | F | F | Bd. | C₃H₇ |
| 258 | F | F | F | F | Bd. | C₃H₇ |
| 259 | F | F | F | F | Bd. | C₄H₉ |
| 260 | H | H | H | H | —CF₂CF₂— | CH₃ |
| 261 | H | H | H | H | —CF₂CF₂— | C₃H₇ |
| 262 | H | H | F | F | —CF₂CF₂— | C₂H₅ |
| 263 | H | H | F | F | —CF₂CF₂— | C₃H₇ |
| 264 | F | F | F | F | —CF₂CF₂— | C₃H₇ |
| 265 | F | F | F | F | —CF₂CF₂— | C₄H₉ |

Bd. = single bond

Examples 266 to 283

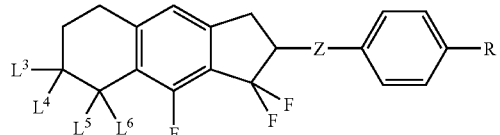

| Example | L³ | L⁴ | L⁵ | L⁶ | Z | R |
|---|---|---|---|---|---|---|
| 266 | H | H | H | H | Bd. | CH₃ |
| 267 | H | H | H | H | Bd. | C₃H₇ |
| 268 | H | H | F | F | Bd. | C₂H₅ |
| 269 | H | H | F | F | Bd. | C₃H₇ |
| 270 | F | F | F | F | Bd. | C₃H₇ |
| 271 | F | F | F | F | Bd. | C₄H₉ |
| 272 | H | H | H | H | —CF₂O— | CH₃ |
| 273 | H | H | H | H | —CF₂O— | C₃H₇ |
| 274 | H | H | F | F | —CF₂O— | C₂H₅ |
| 275 | H | H | F | F | —CF₂O— | C₃H₇ |
| 276 | F | F | F | F | —CF₂O— | C₃H₇ |
| 277 | F | F | F | F | —CF₂O— | C₄H₉ |
| 278 | H | H | H | H | —CF₂CF₂— | CH₃ |
| 279 | H | H | H | H | —CF₂CF₂— | C₃H₇ |
| 280 | H | H | F | F | —CF₂CF₂— | C₂H₅ |
| 281 | H | H | F | F | —CF₂CF₂— | C₃H₇ |
| 282 | F | F | F | F | —CF₂CF₂— | C₃H₇ |
| 283 | F | F | F | F | —CF₂CF₂— | C₄H₉ |

Bd. = single bond

Examples 284 to 301

| Example | L³ | L⁴ | L⁵ | L⁶ | Z | R |
|---|---|---|---|---|---|---|
| 284 | H | H | H | H | Bd. | CH₃ |
| 285 | H | H | H | H | Bd. | C₃H₇ |
| 286 | H | H | F | F | Bd. | C₂H₅ |
| 287 | H | H | F | F | Bd. | C₃H₇ |
| 288 | F | F | F | F | Bd. | C₃H₇ |
| 289 | F | F | F | F | Bd. | C₄H₉ |
| 290 | H | H | H | H | —CF₂O— | CH₃ |
| 291 | H | H | H | H | —CF₂O— | C₃H₇ |
| 292 | H | H | F | F | —CF₂O— | C₂H₅ |
| 293 | H | H | F | F | —CF₂O— | C₃H₇ |
| 294 | F | F | F | F | —CF₂O— | C₃H₇ |
| 295 | F | F | F | F | —CF₂O— | C₄H₉ |
| 296 | H | H | H | H | —CF₂CF₂— | CH₃ |
| 297 | H | H | H | H | —CF₂CF₂— | C₃H₇ |
| 298 | H | H | F | F | —CF₂CF₂— | C₂H₅ |
| 299 | H | H | F | F | —CF₂CF₂— | C₃H₇ |
| 300 | F | F | F | F | —CF₂CF₂— | C₃H₇ |
| 301 | F | F | F | F | —CF₂CF₂— | C₄H₉ |

Bd. = single bond

TABLE 1

Δε and Δn values for substances of individual examples

| Example No. | Δε | Δn |
|---|---|---|
| 17 | −6.3 | 0.143 |
| 18 | −8.0 | 0.143 |
| 20 | −7.3 | 0.166 |
| 79 | −3.9 | 0.127 |
| 81 | −9.1 | 0.117 |
| 82 | −10.2 | 0.121 |
| 143 | −3.3 | 0.091 |
| 145 | −11.8 | 0.081 |
| 146 | −9.2 | 0.081 |
| 207 | −2.2 | 0.128 |
| 209 | −9.6 | 0.115 |
| 210 | −6.9 | 0.106 |
| 255 | −3.0 | 0.095 |
| 257 | −10.3 | 0.079 |
| 258 | −7.9 | 0.079 |

TABLE 2

Δε and Δn values for substances of individual examples

| Example No. | Δε | Δn |
|---|---|---|
| 306 | 12.9 | 0.179 |
| 309 | 17.0 | 0.158 |
| 312 | 12.7 | 0.160 |
| 321 | 23.2 | 0.159 |
| 324 | 12.4 | 0.172 |
| 327 | 31.4 | 0.159 |
| 330 | 19.7 | 0.143 |
| 333 | 17.4 | 0.158 |

Examples 302 to 337

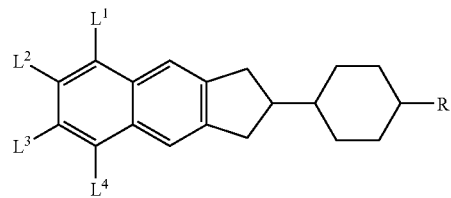

| Example | L¹ | L² | L³ | L⁴ | R |
|---|---|---|---|---|---|
| 302 | H | F | H | H | CH$_3$ |
| 303 | H | F | H | H | C$_3$H$_7$ |
| 304 | H | F | H | H | C$_5$H$_{11}$ |
| 305 | H | F | F | H | C$_2$H$_5$ |
| 306 | H | F | F | H | C$_3$H$_7$ |
| 307 | H | F | F | H | C$_6$H$_{13}$ |
| 308 | F | F | F | F | CH$_3$ |
| 309 | F | F | F | F | C$_3$H$_7$ |
| 310 | F | F | F | F | C$_5$H$_{11}$ |
| 311 | H | CF$_3$ | H | H | C$_2$H$_5$ |
| 312 | H | CF$_3$ | H | H | C$_3$H$_7$ |
| 313 | H | CF$_3$ | H | H | C$_6$H$_{13}$ |
| 314 | H | OCF$_3$ | H | H | CH$_3$ |
| 315 | H | OCF$_3$ | H | H | C$_3$H$_7$ |
| 316 | H | OCF$_3$ | H | H | C$_5$H$_{11}$ |
| 317 | H | CN | H | H | C$_2$H$_5$ |
| 318 | H | CN | H | H | C$_3$H$_7$ |
| 319 | H | CN | H | H | C$_6$H$_{13}$ |
| 320 | H | CF$_3$ | F | H | C$_2$H$_5$ |
| 321 | H | CF$_3$ | F | H | C$_3$H$_7$ |
| 322 | H | CF$_3$ | F | H | C$_6$H$_{13}$ |
| 323 | H | OCF$_3$ | F | H | CH$_3$ |
| 324 | H | OCF$_3$ | F | H | C$_3$H$_7$ |
| 325 | H | OCF$_3$ | F | H | C$_5$H$_{11}$ |
| 326 | H | CF$_3$ | CF$_3$ | H | C$_2$H$_5$ |
| 327 | H | CF$_3$ | CF$_3$ | H | C$_3$H$_7$ |
| 328 | H | CF$_3$ | CF$_3$ | H | C$_6$H$_{13}$ |
| 329 | H | CF$_3$ | OCF$_3$ | H | CH$_3$ |
| 330 | H | CF$_3$ | OCF$_3$ | H | C$_3$H$_7$ |
| 331 | H | CF$_3$ | OCF$_3$ | H | C$_5$H$_{11}$ |
| 332 | H | OCF$_3$ | OCF$_3$ | H | C$_2$H$_5$ |
| 333 | H | OCF$_3$ | OCF$_3$ | H | C$_3$H$_7$ |
| 334 | H | OCF$_3$ | OCF$_3$ | H | C$_6$H$_{13}$ |
| 335 | H | CN | CN | H | C$_2$H$_5$ |
| 336 | H | CN | CN | H | C$_3$H$_7$ |
| 337 | H | CN | CN | H | C$_6$H$_{13}$ |

Examples 338 to 367

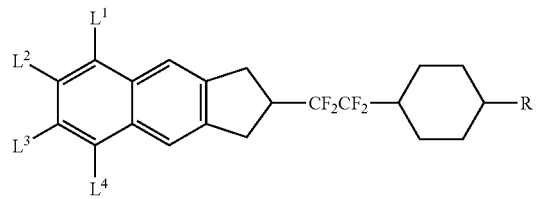

| Example | L¹ | L² | L³ | L⁴ | R |
|---|---|---|---|---|---|
| 338 | H | F | H | H | CH$_3$ |
| 339 | H | F | H | H | C$_3$H$_7$ |
| 340 | H | F | H | H | C$_5$H$_{11}$ |
| 341 | H | F | F | H | C$_2$H$_5$ |
| 342 | H | F | F | H | C$_3$H$_7$ |
| 343 | H | F | F | H | C$_6$H$_{13}$ |
| 344 | F | F | F | F | CH$_3$ |
| 345 | F | F | F | F | C$_3$H$_7$ |
| 346 | F | F | F | F | C$_5$H$_{11}$ |
| 347 | H | CF$_3$ | H | H | C$_2$H$_5$ |
| 348 | H | CF$_3$ | H | H | C$_3$H$_7$ |
| 349 | H | CF$_3$ | H | H | C$_6$H$_{13}$ |
| 350 | H | OCF$_3$ | H | H | CH$_3$ |
| 351 | H | OCF$_3$ | H | H | C$_3$H$_7$ |
| 352 | H | OCF$_3$ | H | H | C$_5$H$_{11}$ |
| 353 | H | CF$_3$ | F | H | C$_2$H$_5$ |
| 354 | H | CF$_3$ | F | H | C$_3$H$_7$ |
| 355 | H | CF$_3$ | F | H | C$_6$H$_{13}$ |
| 356 | H | OCF$_3$ | F | H | CH$_3$ |
| 357 | H | OCF$_3$ | F | H | C$_3$H$_7$ |
| 358 | H | OCF$_3$ | F | H | C$_5$H$_{11}$ |
| 359 | H | CF$_3$ | CF$_3$ | H | C$_2$H$_5$ |
| 360 | H | CF$_3$ | CF$_3$ | H | C$_3$H$_7$ |
| 361 | H | CF$_3$ | CF$_3$ | H | C$_6$H$_{13}$ |
| 362 | H | CF$_3$ | OCF$_3$ | H | CH$_3$ |
| 363 | H | CF$_3$ | OCF$_3$ | H | C$_3$H$_7$ |
| 364 | H | CF$_3$ | OCF$_3$ | H | C$_5$H$_{11}$ |
| 365 | H | OCF$_3$ | OCF$_3$ | H | C$_2$H$_5$ |
| 366 | H | OCF$_3$ | OCF$_3$ | H | C$_3$H$_7$ |
| 367 | H | OCF$_3$ | OCF$_3$ | H | C$_6$H$_{13}$ |

Examples 368 to 397

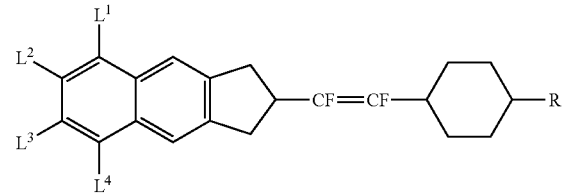

| Example | L¹ | L² | L³ | L⁴ | R |
|---|---|---|---|---|---|
| 368 | H | F | H | H | CH₃ |
| 369 | H | F | H | H | C₃H₇ |
| 370 | H | F | H | H | C₅H₁₁ |
| 371 | H | F | F | H | C₂H₅ |
| 372 | H | F | F | H | C₃H₇ |
| 373 | H | F | F | H | C₆H₁₃ |
| 374 | F | F | F | F | CH₃ |
| 375 | F | F | F | F | C₃H₇ |
| 376 | F | F | F | F | C₅H₁₁ |
| 377 | H | CF₃ | H | H | C₂H₅ |
| 378 | H | CF₃ | H | H | C₃H₇ |
| 379 | H | CF₃ | H | H | C₆H₁₃ |
| 380 | H | OCF₃ | H | H | CH₃ |
| 381 | H | OCF₃ | H | H | C₃H₇ |
| 382 | H | OCF₃ | H | H | C₅H₁₁ |
| 383 | H | CF₃ | F | H | C₂H₅ |
| 384 | H | CF₃ | F | H | C₃H₇ |
| 385 | H | CF₃ | F | H | C₆H₁₃ |
| 386 | H | OCF₃ | F | H | CH₃ |
| 387 | H | OCF₃ | F | H | C₃H₇ |
| 388 | H | OCF₃ | F | H | C₅H₁₁ |
| 389 | H | CF₃ | CF₃ | H | C₂H₅ |
| 390 | H | CF₃ | CF₃ | H | C₃H₇ |
| 391 | H | CF₃ | CF₃ | H | C₆H₁₃ |
| 392 | H | CF₃ | OCF₃ | H | CH₃ |
| 393 | H | CF₃ | OCF₃ | H | C₃H₇ |
| 394 | H | CF₃ | OCF₃ | H | C₅H₁₁ |
| 395 | H | OCF₃ | OCF₃ | H | C₂H₅ |
| 396 | H | OCF₃ | OCF₃ | H | C₃H₇ |
| 397 | H | OCF₃ | OCF₃ | H | C₆H₁₃ |

Examples 398 to 427

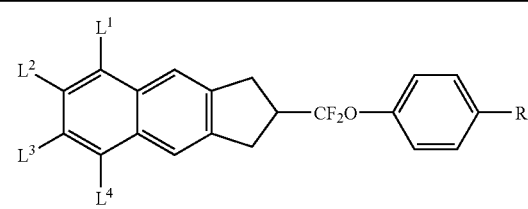

| Example | L¹ | L² | L³ | L⁴ | R |
|---|---|---|---|---|---|
| 398 | H | F | H | H | CH₃ |
| 399 | H | F | H | H | C₃H₇ |
| 400 | H | F | H | H | C₅H₁₁ |
| 401 | H | F | F | H | C₂H₅ |
| 402 | H | F | F | H | C₃H₇ |
| 403 | H | F | F | H | C₆H₁₃ |
| 404 | F | F | F | F | CH₃ |
| 405 | F | F | F | F | C₃H₇ |
| 406 | F | F | F | F | C₅H₁₁ |
| 407 | H | CF₃ | H | H | C₂H₅ |
| 408 | H | CF₃ | H | H | C₃H₇ |
| 409 | H | CF₃ | H | H | C₆H₁₃ |
| 410 | H | OCF₃ | H | H | CH₃ |
| 411 | H | OCF₃ | H | H | C₃H₇ |
| 412 | H | OCF₃ | H | H | C₅H₁₁ |
| 413 | H | CF₃ | F | H | C₂H₅ |
| 414 | H | CF₃ | F | H | C₃H₇ |
| 415 | H | CF₃ | F | H | C₆H₁₃ |
| 416 | H | OCF₃ | F | H | CH₃ |
| 417 | H | OCF₃ | F | H | C₃H₇ |
| 418 | H | OCF₃ | F | H | C₅H₁₁ |
| 419 | H | CF₃ | CF₃ | H | C₂H₅ |
| 420 | H | CF₃ | CF₃ | H | C₃H₇ |
| 421 | H | CF₃ | CF₃ | H | C₆H₁₃ |
| 422 | H | CF₃ | OCF₃ | H | CH₃ |
| 423 | H | CF₃ | OCF₃ | H | C₃H₇ |
| 424 | H | CF₃ | OCF₃ | H | C₅H₁₁ |
| 425 | H | OCF₃ | OCF₃ | H | C₂H₅ |
| 426 | H | OCF₃ | OCF₃ | H | C₃H₇ |
| 427 | H | OCF₃ | OCF₃ | H | C₆H₁₃ |

Examples 428 to 457

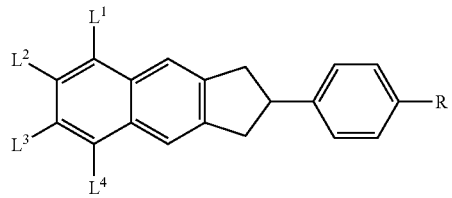

| Example | L¹ | L² | L³ | L⁴ | R |
|---|---|---|---|---|---|
| 428 | H | F | H | H | CH₃ |
| 429 | H | F | H | H | C₃H₇ |
| 430 | H | F | H | H | C₅H₁₁ |
| 431 | H | F | F | H | C₂H₅ |
| 432 | H | F | F | H | C₃H₇ |
| 433 | H | F | F | H | C₆H₁₃ |
| 434 | F | F | F | F | CH₃ |
| 435 | F | F | F | F | C₃H₇ |
| 436 | F | F | F | F | C₅H₁₁ |
| 437 | H | CF₃ | H | H | C₂H₅ |
| 438 | H | CF₃ | H | H | C₃H₇ |
| 439 | H | CF₃ | H | H | C₆H₁₃ |
| 440 | H | OCF₃ | H | H | CH₃ |
| 441 | H | OCF₃ | H | H | C₃H₇ |
| 442 | H | OCF₃ | H | H | C₅H₁₁ |
| 443 | H | CF₃ | F | H | C₂H₅ |
| 444 | H | CF₃ | F | H | C₃H₇ |
| 445 | H | CF₃ | F | H | C₆H₁₃ |
| 446 | H | OCF₃ | F | H | CH₃ |
| 447 | H | OCF₃ | F | H | C₃H₇ |
| 448 | H | OCF₃ | F | H | C₅H₁₁ |
| 449 | H | CF₃ | CF₃ | H | C₂H₅ |
| 450 | H | CF₃ | CF₃ | H | C₃H₇ |
| 451 | H | CF₃ | CF₃ | H | C₆H₁₃ |
| 452 | H | CF₃ | OCF₃ | H | CH₃ |
| 453 | H | CF₃ | OCF₃ | H | C₃H₇ |
| 454 | H | CF₃ | OCF₃ | H | C₅H₁₁ |
| 455 | H | OCF₃ | OCF₃ | H | C₂H₅ |

-continued

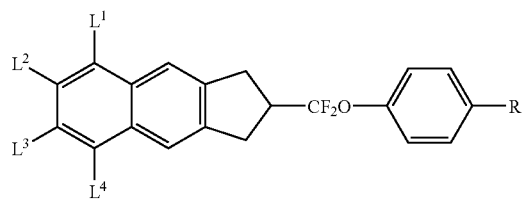

| Example | L¹ | L² | L³ | L⁴ | R |
|---|---|---|---|---|---|
| 456 | H | OCF₃ | OCF₃ | H | C₃H₇ |
| 457 | H | OCF₃ | OCF₃ | H | C₆H₁₃ |

Examples 458 to 487

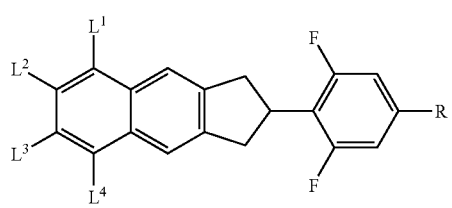

| Example | L¹ | L² | L³ | L⁴ | R |
|---|---|---|---|---|---|
| 458 | H | F | H | H | CH₃ |
| 459 | H | F | H | H | C₃H₇ |
| 460 | H | F | H | H | C₅H₁₁ |
| 461 | H | F | F | H | C₂H₅ |
| 462 | H | F | F | H | C₃H₇ |
| 463 | H | F | F | H | C₆H₁₃ |
| 464 | F | F | F | F | CH₃ |
| 465 | F | F | F | F | C₃H₇ |
| 466 | F | F | F | F | C₅H₁₁ |
| 467 | H | CF₃ | H | H | C₂H₅ |
| 468 | H | CF₃ | H | H | C₃H₇ |
| 469 | H | CF₃ | H | H | C₆H₁₃ |
| 470 | H | OCF₃ | H | H | CH₃ |
| 471 | H | OCF₃ | H | H | C₃H₇ |
| 472 | H | OCF₃ | H | H | C₅H₁₁ |
| 473 | H | CF₃ | F | H | C₂H₅ |
| 474 | H | CF₃ | F | H | C₃H₇ |
| 475 | H | CF₃ | F | H | C₆H₁₃ |
| 476 | H | OCF₃ | F | H | CH₃ |
| 477 | H | OCF₃ | F | H | C₃H₇ |
| 478 | H | OCF₃ | F | H | C₅H₁₁ |
| 479 | H | CF₃ | CF₃ | H | C₂H₅ |
| 480 | H | CF₃ | CF₃ | H | C₃H₇ |
| 481 | H | CF₃ | CF₃ | H | C₆H₁₃ |
| 482 | H | CF₃ | OCF₃ | H | CH₃ |
| 483 | H | CF₃ | OCF₃ | H | C₃H₇ |
| 484 | H | CF₃ | OCF₃ | H | C₅H₁₁ |
| 485 | H | OCF₃ | OCF₃ | H | C₂H₅ |
| 486 | H | OCF₃ | OCF₃ | H | C₃H₇ |
| 487 | H | OCF₃ | OCF₃ | H | C₆H₁₃ |

Examples 488 to 517

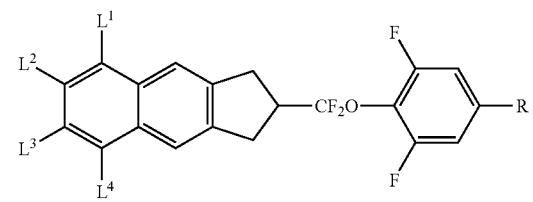

| Example | L¹ | L² | L³ | L⁴ | R |
|---|---|---|---|---|---|
| 488 | H | F | H | H | CH₃ |
| 489 | H | F | H | H | C₃H₇ |
| 490 | H | F | H | H | C₅H₁₁ |
| 491 | H | F | F | H | C₂H₅ |
| 492 | H | F | F | H | C₃H₇ |
| 493 | H | F | F | H | C₆H₁₃ |
| 494 | F | F | F | F | CH₃ |
| 495 | F | F | F | F | C₃H₇ |
| 496 | F | F | F | F | C₅H₁₁ |
| 497 | H | CF₃ | H | H | C₂H₅ |
| 498 | H | CF₃ | H | H | C₃H₇ |
| 499 | H | CF₃ | H | H | C₆H₁₃ |
| 500 | H | OCF₃ | H | H | CH₃ |
| 501 | H | OCF₃ | H | H | C₃H₇ |
| 502 | H | OCF₃ | H | H | C₅H₁₁ |
| 503 | H | CF₃ | F | H | C₂H₅ |
| 504 | H | CF₃ | F | H | C₃H₇ |
| 505 | H | CF₃ | F | H | C₆H₁₃ |
| 506 | H | OCF₃ | F | H | CH₃ |
| 507 | H | OCF₃ | F | H | C₃H₇ |
| 508 | H | OCF₃ | F | H | C₅H₁₁ |
| 509 | H | CF₃ | CF₃ | H | C₂H₅ |
| 510 | H | CF₃ | CF₃ | H | C₃H₇ |
| 511 | H | CF₃ | CF₃ | H | C₆H₁₃ |
| 512 | H | CF₃ | OCF₃ | H | CH₃ |
| 513 | H | CF₃ | OCF₃ | H | C₃H₇ |
| 514 | H | CF₃ | OCF₃ | H | C₅H₁₁ |
| 515 | H | OCF₃ | OCF₃ | H | C₂H₅ |
| 516 | H | OCF₃ | OCF₃ | H | C₃H₇ |
| 517 | H | OCF₃ | OCF₃ | H | C₆H₁₃ |

Examples 518 to 547

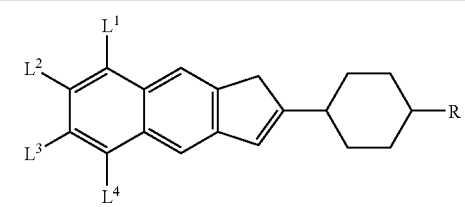

| Example | L¹ | L² | L³ | L⁴ | R |
|---|---|---|---|---|---|
| 518 | H | F | H | H | CH₃ |
| 519 | H | F | H | H | C₃H₇ |
| 520 | H | F | H | H | C₅H₁₁ |
| 521 | H | F | F | H | C₂H₅ |
| 522 | H | F | F | H | C₃H₇ |
| 523 | H | F | F | H | C₆H₁₃ |
| 524 | F | F | F | F | CH₃ |
| 525 | F | F | F | F | C₃H₇ |
| 526 | F | F | F | F | C₅H₁₁ |
| 527 | H | CF₃ | H | H | C₂H₅ |
| 528 | H | CF₃ | H | H | C₃H₇ |
| 529 | H | CF₃ | H | H | C₆H₁₃ |
| 530 | H | OCF₃ | H | H | CH₃ |

-continued

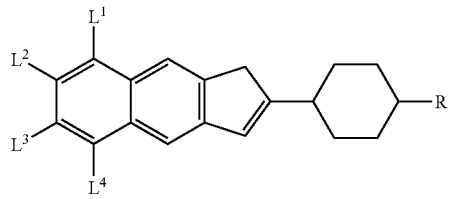

| Example | L¹ | L² | L³ | L⁴ | R |
|---|---|---|---|---|---|
| 531 | H | OCF₃ | H | H | C₃H₇ |
| 532 | H | OCF₃ | H | H | C₅H₁₁ |
| 533 | H | CF₃ | F | H | C₂H₅ |
| 534 | H | CF₃ | F | H | C₃H₇ |
| 535 | H | CF₃ | F | H | C₆H₁₃ |
| 536 | H | OCF₃ | F | H | CH₃ |
| 537 | H | OCF₃ | F | H | C₃H₇ |
| 538 | H | OCF₃ | F | H | C₅H₁₁ |
| 539 | H | CF₃ | CF₃ | H | C₂H₅ |
| 540 | H | CF₃ | CF₃ | H | C₃H₇ |
| 541 | H | CF₃ | CF₃ | H | C₆H₁₃ |
| 542 | H | CF₃ | OCF₃ | H | CH₃ |
| 543 | H | CF₃ | OCF₃ | H | C₃H₇ |
| 544 | H | CF₃ | OCF₃ | H | C₅H₁₁ |
| 545 | H | OCF₃ | OCF₃ | H | C₂H₅ |
| 546 | H | OCF₃ | OCF₃ | H | C₃H₇ |
| 547 | H | OCF₃ | OCF₃ | H | C₆H₁₃ |

Examples 548 to 577

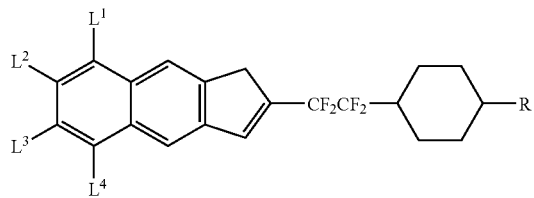

| Example | L¹ | L² | L³ | L⁴ | R |
|---|---|---|---|---|---|
| 548 | H | F | H | H | CH₃ |
| 549 | H | F | H | H | C₃H₇ |
| 550 | H | F | H | H | C₅H₁₁ |
| 551 | H | F | F | H | C₂H₅ |
| 552 | H | F | F | H | C₃H₇ |
| 553 | H | F | F | H | C₆H₁₃ |
| 554 | F | F | F | F | CH₃ |
| 555 | F | F | F | F | C₃H₇ |
| 556 | F | F | F | F | C₅H₁₁ |
| 557 | H | CF₃ | H | H | C₂H₅ |
| 558 | H | CF₃ | H | H | C₃H₇ |
| 559 | H | CF₃ | H | H | C₆H₁₃ |
| 560 | H | OCF₃ | H | H | CH₃ |
| 561 | H | OCF₃ | H | H | C₃H₇ |
| 562 | H | OCF₃ | H | H | C₅H₁₁ |
| 563 | H | CF₃ | F | H | C₂H₅ |
| 564 | H | CF₃ | F | H | C₃H₇ |
| 565 | H | CF₃ | F | H | C₆H₁₃ |
| 566 | H | OCF₃ | F | H | CH₃ |
| 567 | H | OCF₃ | F | H | C₃H₇ |
| 568 | H | OCF₃ | F | H | C₅H₁₁ |
| 569 | H | CF₃ | CF₃ | H | C₂H₅ |
| 570 | H | CF₃ | CF₃ | H | C₃H₇ |
| 571 | H | CF₃ | CF₃ | H | C₆H₁₃ |
| 572 | H | CF₃ | OCF₃ | H | CH₃ |
| 573 | H | CF₃ | OCF₃ | H | C₃H₇ |
| 574 | H | CF₃ | OCF₃ | H | C₅H₁₁ |
| 575 | H | OCF₃ | OCF₃ | H | C₂H₅ |

-continued

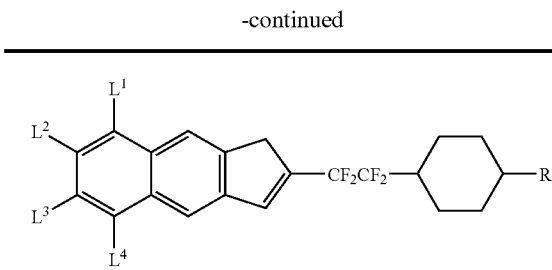

| Example | L¹ | L² | L³ | L⁴ | R |
|---|---|---|---|---|---|
| 576 | H | OCF₃ | OCF₃ | H | C₃H₇ |
| 577 | H | OCF₃ | OCF₃ | H | C₆H₁₃ |

Examples 578 to 607

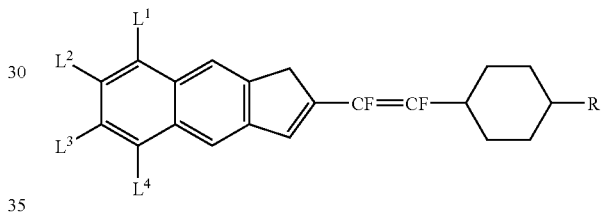

| Example | L¹ | L² | L³ | L⁴ | R |
|---|---|---|---|---|---|
| 578 | H | F | H | H | CH₃ |
| 579 | H | F | H | H | C₃H₇ |
| 580 | H | F | H | H | C₅H₁₁ |
| 581 | H | F | F | H | C₂H₅ |
| 582 | H | F | F | H | C₃H₇ |
| 583 | H | F | F | H | C₆H₁₃ |
| 584 | F | F | F | F | CH₃ |
| 585 | F | F | F | F | C₃H₇ |
| 586 | F | F | F | F | C₅H₁₁ |
| 587 | H | CF₃ | H | H | C₂H₅ |
| 588 | H | CF₃ | H | H | C₃H₇ |
| 589 | H | CF₃ | H | H | C₆H₁₃ |
| 590 | H | OCF₃ | H | H | CH₃ |
| 591 | H | OCF₃ | H | H | C₃H₇ |
| 592 | H | OCF₃ | H | H | C₅H₁₁ |
| 593 | H | CF₃ | F | H | C₂H₅ |
| 594 | H | CF₃ | F | H | C₃H₇ |
| 595 | H | CF₃ | F | H | C₆H₁₃ |
| 596 | H | OCF₃ | F | H | CH₃ |
| 597 | H | OCF₃ | F | H | C₃H₇ |
| 598 | H | OCF₃ | F | H | C₅H₁₁ |
| 599 | H | CF₃ | CF₃ | H | C₂H₅ |
| 600 | H | CF₃ | CF₃ | H | C₃H₇ |
| 601 | H | CF₃ | CF₃ | H | C₆H₁₃ |
| 602 | H | CF₃ | OCF₃ | H | CH₃ |
| 603 | H | CF₃ | OCF₃ | H | C₃H₇ |
| 604 | H | CF₃ | OCF₃ | H | C₅H₁₁ |
| 605 | H | OCF₃ | OCF₃ | H | C₂H₅ |
| 606 | H | OCF₃ | OCF₃ | H | C₃H₇ |
| 607 | H | OCF₃ | OCF₃ | H | C₆H₁₃ |

Examples 608 to 637

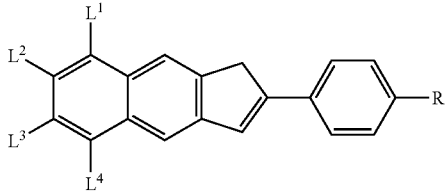

| Example | L¹ | L² | L³ | L⁴ | R |
|---|---|---|---|---|---|
| 608 | H | F | H | H | $CH_3$ |
| 609 | H | F | H | H | $C_3H_7$ |
| 610 | H | F | H | H | $C_5H_{11}$ |
| 611 | H | F | F | H | $C_2H_5$ |
| 612 | H | F | F | H | $C_3H_7$ |
| 613 | H | F | F | H | $C_6H_{13}$ |
| 614 | F | F | F | F | $CH_3$ |
| 615 | F | F | F | F | $C_3H_7$ |
| 616 | F | F | F | F | $C_5H_{11}$ |
| 617 | H | $CF_3$ | H | H | $C_2H_5$ |
| 618 | H | $CF_3$ | H | H | $C_3H_7$ |
| 619 | H | $CF_3$ | H | H | $C_6H_{13}$ |
| 620 | H | $OCF_3$ | H | H | $CH_3$ |
| 621 | H | $OCF_3$ | H | H | $C_3H_7$ |
| 622 | H | $OCF_3$ | H | H | $C_5H_{11}$ |
| 623 | H | $CF_3$ | F | H | $C_2H_5$ |
| 624 | H | $CF_3$ | F | H | $C_3H_7$ |
| 625 | H | $CF_3$ | F | H | $C_6H_{13}$ |
| 626 | H | $OCF_3$ | F | H | $CH_3$ |
| 627 | H | $OCF_3$ | F | H | $C_3H_7$ |
| 628 | H | $OCF_3$ | F | H | $C_5H_{11}$ |
| 629 | H | $CF_3$ | $CF_3$ | H | $C_2H_5$ |
| 630 | H | $CF_3$ | $CF_3$ | H | $C_3H_7$ |
| 631 | H | $CF_3$ | $CF_3$ | H | $C_6H_{13}$ |
| 632 | H | $CF_3$ | $OCF_3$ | H | $CH_3$ |
| 633 | H | $CF_3$ | $OCF_3$ | H | $C_3H_7$ |
| 634 | H | $CF_3$ | $OCF_3$ | H | $C_5H_{11}$ |
| 635 | H | $OCF_3$ | $OCF_3$ | H | $C_2H_5$ |
| 636 | H | $OCF_3$ | $OCF_3$ | H | $C_3H_7$ |
| 637 | H | $OCF_3$ | $OCF_3$ | H | $C_6H_{13}$ |

Examples 638 to 667

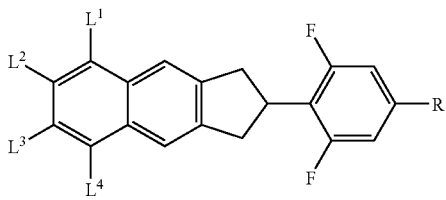

| Example | L¹ | L² | L³ | L⁴ | R |
|---|---|---|---|---|---|
| 638 | H | F | H | H | $CH_3$ |
| 639 | H | F | H | H | $C_3H_7$ |
| 640 | H | F | H | H | $C_5H_{11}$ |
| 641 | H | F | F | H | $C_2H_5$ |
| 642 | H | F | F | H | $C_3H_7$ |
| 643 | H | F | F | H | $C_6H_{13}$ |
| 644 | F | F | F | F | $CH_3$ |
| 645 | F | F | F | F | $C_3H_7$ |
| 646 | F | F | F | F | $C_5H_{11}$ |
| 647 | H | $CF_3$ | H | H | $C_2H_5$ |
| 648 | H | $CF_3$ | H | H | $C_3H_7$ |
| 649 | H | $CF_3$ | H | H | $C_6H_{13}$ |
| 650 | H | $OCF_3$ | H | H | $CH_3$ |

-continued

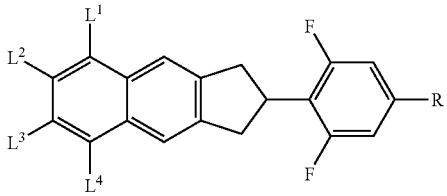

| Example | L¹ | L² | L³ | L⁴ | R |
|---|---|---|---|---|---|
| 651 | H | $OCF_3$ | H | H | $C_3H_7$ |
| 652 | H | $OCF_3$ | H | H | $C_5H_{11}$ |
| 653 | H | $CF_3$ | F | H | $C_2H_5$ |
| 654 | H | $CF_3$ | F | H | $C_3H_7$ |
| 655 | H | $CF_3$ | F | H | $C_6H_{13}$ |
| 656 | H | $OCF_3$ | F | H | $CH_3$ |
| 657 | H | $OCF_3$ | F | H | $C_3H_7$ |
| 658 | H | $OCF_3$ | F | H | $C_5H_{11}$ |
| 659 | H | $CF_3$ | $CF_3$ | H | $C_2H_5$ |
| 660 | H | $CF_3$ | $CF_3$ | H | $C_3H_7$ |
| 661 | H | $CF_3$ | $CF_3$ | H | $C_6H_{13}$ |
| 662 | H | $CF_3$ | $OCF_3$ | H | $CH_3$ |
| 663 | H | $CF_3$ | $OCF_3$ | H | $C_3H_7$ |
| 664 | H | $CF_3$ | $OCF_3$ | H | $C_5H_{11}$ |
| 665 | H | $OCF_3$ | $OCF_3$ | H | $C_2H_5$ |
| 666 | H | $OCF_3$ | $OCF_3$ | H | $C_3H_7$ |
| 667 | H | $OCF_3$ | $OCF_3$ | H | $C_6H_{13}$ |

Examples 668 to 697

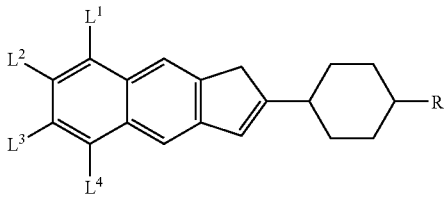

| Example | L¹ | L² | L³ | L⁴ | R |
|---|---|---|---|---|---|
| 668 | H | F | H | H | $CH_3$ |
| 669 | H | F | H | H | $C_3H_7$ |
| 670 | H | F | H | H | $C_5H_{11}$ |
| 671 | H | F | F | H | $C_2H_5$ |
| 672 | H | F | F | H | $C_3H_7$ |
| 673 | H | F | F | H | $C_6H_{13}$ |
| 674 | F | F | F | F | $CH_3$ |
| 675 | F | F | F | F | $C_3H_7$ |
| 676 | F | F | F | F | $C_5H_{11}$ |
| 677 | H | $CF_3$ | H | H | $C_2H_5$ |
| 678 | H | $CF_3$ | H | H | $C_3H_7$ |
| 679 | H | $CF_3$ | H | H | $C_6H_{13}$ |
| 680 | H | $OCF_3$ | H | H | $CH_3$ |
| 681 | H | $OCF_3$ | H | H | $C_3H_7$ |
| 682 | H | $OCF_3$ | H | H | $C_5H_{11}$ |
| 683 | H | $CF_3$ | F | H | $C_2H_5$ |
| 684 | H | $CF_3$ | F | H | $C_3H_7$ |
| 685 | H | $CF_3$ | F | H | $C_6H_{13}$ |
| 686 | H | $OCF_3$ | F | H | $CH_3$ |
| 687 | H | $OCF_3$ | F | H | $C_3H_7$ |
| 688 | H | $OCF_3$ | F | H | $C_5H_{11}$ |
| 689 | H | $CF_3$ | $CF_3$ | H | $C_2H_5$ |
| 690 | H | $CF_3$ | $CF_3$ | H | $C_3H_7$ |
| 691 | H | $CF_3$ | $CF_3$ | H | $C_6H_{13}$ |
| 692 | H | $CF_3$ | $OCF_3$ | H | $CH_3$ |
| 693 | H | $CF_3$ | $OCF_3$ | H | $C_3H_7$ |
| 694 | H | $CF_3$ | $OCF_3$ | H | $C_5H_{11}$ |
| 695 | H | $OCF_3$ | $OCF_3$ | H | $C_2H_5$ |

-continued

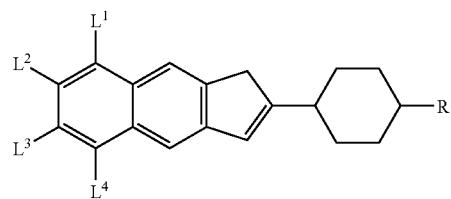

| Example | L¹ | L² | L³ | L⁴ | R |
|---|---|---|---|---|---|
| 696 | H | OCF₃ | OCF₃ | H | C₃H₇ |
| 697 | H | OCF₃ | OCF₃ | H | C₆H₁₃ |

Examples 698 to 727

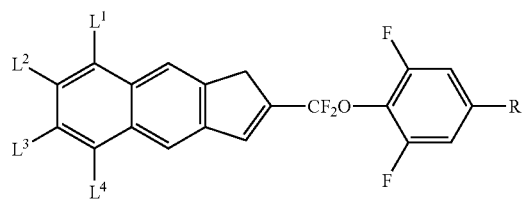

| Example | L¹ | L² | L³ | L⁴ | R |
|---|---|---|---|---|---|
| 698 | H | F | H | H | CH₃ |
| 699 | H | F | H | H | C₃H₇ |
| 700 | H | F | H | H | C₅H₁₁ |
| 701 | H | F | F | H | C₂H₅ |
| 702 | H | F | F | H | C₃H₇ |
| 703 | H | F | F | H | C₆H₁₃ |
| 704 | F | F | F | F | CH₃ |
| 705 | F | F | F | F | C₃H₇ |
| 706 | F | F | F | F | C₅H₁₁ |
| 707 | H | CF₃ | H | H | C₂H₅ |
| 708 | H | CF₃ | H | H | C₃H₇ |
| 709 | H | CF₃ | H | H | C₆H₁₃ |
| 710 | H | OCF₃ | H | H | CH₃ |
| 711 | H | OCF₃ | H | H | C₃H₇ |
| 712 | H | OCF₃ | H | H | C₅H₁₁ |
| 713 | H | CF₃ | F | H | C₂H₅ |
| 714 | H | CF₃ | F | H | C₃H₇ |
| 715 | H | CF₃ | F | H | C₆H₁₃ |
| 716 | H | OCF₃ | F | H | CH₃ |
| 717 | H | OCF₃ | F | H | C₃H₇ |
| 718 | H | OCF₃ | F | H | C₅H₁₁ |
| 719 | H | CF₃ | CF₃ | H | C₂H₅ |
| 720 | H | CF₃ | CF₃ | H | C₃H₇ |
| 721 | H | CF₃ | CF₃ | H | C₆H₁₃ |
| 722 | H | CF₃ | OCF₃ | H | CH₃ |
| 723 | H | CF₃ | OCF₃ | H | C₃H₇ |
| 724 | H | CF₃ | OCF₃ | H | C₅H₁₁ |
| 725 | H | OCF₃ | OCF₃ | H | C₂H₅ |
| 726 | H | OCF₃ | OCF₃ | H | C₃H₇ |
| 727 | H | OCF₃ | OCF₃ | H | C₆H₁₃ |

What is claimed is:

1. A cyclopenta [b]naphthalene compound of formula (I)

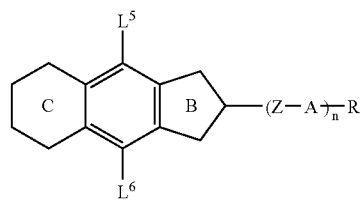

in which:

C is 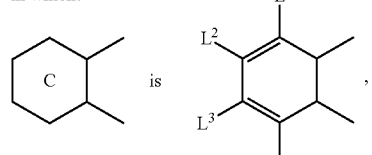

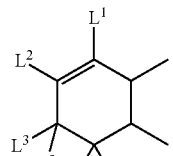

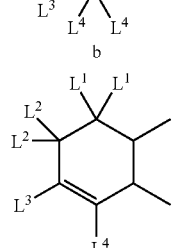

B is 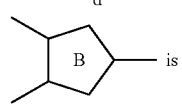

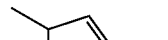

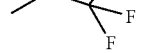

or 

Z is in each case, independently of one another, a single bond, a double bond, —CF₂O—, —OCF₂—, —CH₂CH₂—, —CF₂CF₂—, —C(O)O—, —OC(O)—, —CH₂O—, —OCH₂—, —CF=CH—, —CH=CF—, —CF=CF—, —CH=CH— or —C≡C—, A is in each case, independently of one another, 1,4-phenylene, in which =CH— may be replaced once or twice by =N—, and which may be monosubstituted to tetrasubstituted, independently of one another, by halogen (—F, —Cl, —Br, —I), —CN, —CH₃, —CH₂F, —CHF₂, —CF₃, —OCH₃, —OCH₂F, —OCHF₂ or —OCF₃, 1,4-cyclohexylene, 1,4-cyclohexenylene or 1,4-cyclohexadienylene, in which —CH₂— may be replaced once or twice, independently of one another, by —O— or —S— in such a way that heteroatoms are not directly adjacent, and which may be monosubstituted or polysubstituted by halogen, or is 1,3-cyclobutylene or bicyclo[2.2.2]octane, R is hydrogen, an alkyl, alkoxy, alkenyl or alkynyl radical having from 1 to 15 or 2 to 15 carbon atoms respectively which is unsubstituted, monosubstituted by —CF₃ or at least monosubstituted by halogen, where, in addition, one or more CH₂ groups in these radicals may each, independently of one another, be replaced by —O—, —S—, —CO—, —COO—, —OCO— or —OCO—O— in such a way that heteroatoms are not directly adjacent, halogen, —CN, —SCN, —NCS, —SF₅, —CF₃, —OCF₃, —OCHF₂ or —OCH₂F, n is 0, 1, 2 or 3, and L¹-L⁶ are each, independently of one another, hydrogen, an alkyl, alkoxy, alkenyl or alkynyl radical having from 1 to 15 or 2 to 15 carbon atoms respectively which is unsubstituted or at least monosubstituted by halogen, where, in addition, one or more CH₂ groups in these radicals may each, independently of one another, be replaced by —O—, —S—, —CO—, —COO—, —OCO— or —OCO—O—in such a way that heteroatoms are not directly adjacent, halogen, —CN, —SCN, —NCS, —SF₅, —CF₃, —OCF₃, —OCHF₂, —OCH₂F or —(Z-A-)ₙ—R.

2. A cyclopenta[b]aphthalene compound according to claim 1 of formulae (II) to (VI)

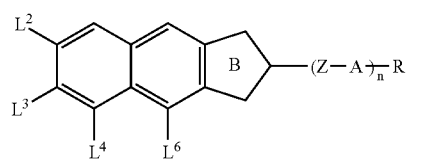
(II)

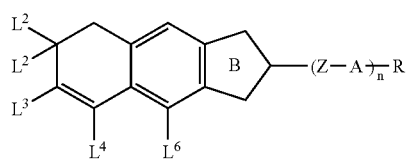
(III)

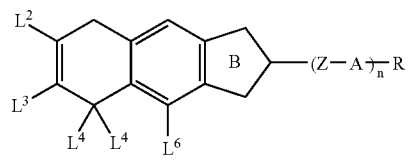
(IV)

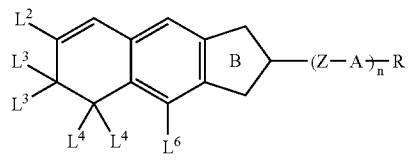
(V)

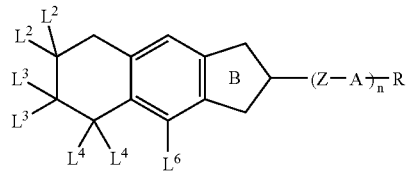
(VI)

Z is in each case, independently of one another, a single bond, a double bond, —CF₂O—, —OCF₂—, —CH₂CH₂—, —CF₂CF₂—, —C(O)O—, —OC(O)—, —CH₂O—, —OCH₂—, —CF=CH—, —CH=CF—, —CF=CF—, —CH=CH— or —C≡C—, A is in each case, independently of one another, 1,4—phenylene, in which =CH— may be replaced once or twice by =N—, and which may be monosubstituted to tetrasubstituted, independently of one another, by halogen (—F, —Cl, —Br, —I), —CN, —CH₃, —CH₂F, —CHF₂, —CF₃, —OCH₃, —OCH₂F, —OCHF₂ or —OCF₃, 1,4-cyclohexylene, 1,4-cyclohexenylene or 1,4-cyclohexadienylene, in which —CH₂— may be replaced once or twice, independently of one another, by —O— or —S— in such a way that heteroatoms are not directly adjacent, and which may be monosubstituted or polysubstituted by halogen, or is 1,3-cyclobutylene or bicyclo[2.2.2]octane, R is hydrogen, an alkyl, alkoxy, alkenyl or alkynyl radical having from 1 to 15 or 2 to 15 carbon atoms respectively which is unsubstituted, monosubstituted by —CF₃ or at least monosubstituted by halogen, where, in addition, one or more CH₂ groups in these radicals may each, independently of one another, be replaced by —O—, —S—, —CO—, —COO—, —OCO— or —OCO—O— in such a way that heteroatoms are not directly adjacent, halogen, —CN, —SCN, —NCS, —SF₅, —CF₃, —OCF₃, —OCHF₂ or —OCH₂F, L², L³ are each, independently of one another, hydrogen, an alkyl, alkoxy, alkenyl or alkynyl radical having from 1 to 15 or 2 to 15 carbon atoms respectively which is unsubstituted or at least monosubstituted by halogen, where, in addition, one or more CH₂ groups in these radicals may each, independently of one another, be replaced by —O—, —S—, —CO—, —COO—, —OCO—or —OCO—O— in such a way that heteroatoms are not directly adjacent, halogen, —CN, —SCN, —NCS, —SF₅, —CF₃, —OCF₃, —OCHF₂, —OCH₂F or -(Z-A-)ₙ-R, L⁴ and L⁶ are each, independently of one another, hydrogen, an alkyl, alkoxy, alkenyl or alkynyl radical having from 1 to 15 or 2 to 15 carbon atoms respectively which is at least monosubstituted by halogen, where, in addition, one or more CH₂ groups in these radicals may each, independently of one another, be replaced by —O—, —S—, —CO—, —COO—, —OCO— or —OCO—O— in such a way that heteroatoms are not directly adjacent, halogen, —CN, —SF₅, —SCN, —NCS, —CF3, —OCF₃, —OCHF₂ or —OCH₂F, preferably with the proviso that L⁴ L⁶ cannot simultaneously be hydrogen, and n is 0, 1, 2 or 3.

3. A cyclopenta[b]naphthalene compound according to claim 2, wherein A is

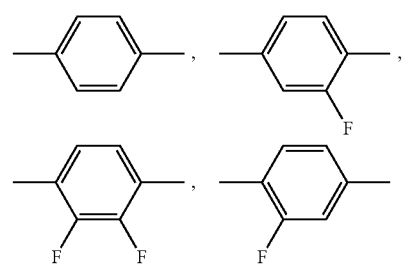

-continued

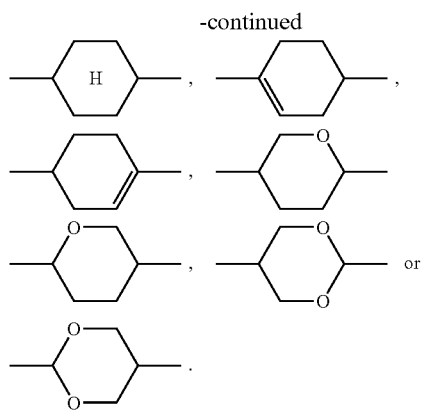

4. A cyclopenta[b]naphthalene compound according to claim 2, wherein $L^2$ and $L^3$, independently of one another, are hydrogen, an alkoxy radical having from 1 to 7 carbon atoms, fluorine or chlorine.

5. A cyclopenta[b]naphthalene compound according to claim 2, wherein $L^4$ and $L^6$, independently of one another, are —$CF_3$, fluorine or chlorine.

6. A cyclopenta[b]naphthalene compound according to claim 1, wherein Z is a single bond, —$CF_2O$—, —$OCF_2$—, —$CF_2CF_2$—, —CH=CH—, —CF=CH—, —CH=CF— or —CF=CF—.

7. A cyclopenta[b]naphthalene compound according to claim 1, wherein R is an alkyl radical, alkoxy radical or alkenyl radical having from 1 to 7 or 2 to 7 carbon atoms respectively.

8. A liquid crystalline medium comprising at least two liquid-crystalline compounds, wherein at least one compound is a cyclopenta[b]naphthalene compound according to claim 1.

9. An Electro optical display element containing a liquid-crystalline medium according to claim 8.

10. A mesogenic liquid crystalline medium, comprising at least one cyclopenta[b]naphthalene compound according to claim 1.

11. An Electro- optical light-control element which contains an electrode arrangement, at least one element for polarisation of light and a mesogenic control medium, where the light-control element is operated at a temperature at which the mesogenic control medium in the unaddressed state is in the isotropic phase, characterised in that the mesogenic control medium comprises at least one cyclopenta[b]naphthalene derivative according to claim 1.

* * * * *

UNITED STATES PATENT AND TRADEMARK OFFICE
CERTIFICATE OF CORRECTION

PATENT NO. : 7,291,366 B2
APPLICATION NO. : 10/524846
DATED : November 6, 2007
INVENTOR(S) : Lars Lietzau It is certified that error appears in the above-identified patent and that said Letters Patent is hereby corrected as shown below:

Column 56, line 58, reads "-C=C-," should read -- -C≡C-, --

Column 58, line 5, reads "=CH-may" should read -- =CH- may --

Column 58, line 29, reads "$L^2$, $L^3$ are each," should read -- $L^2$ and $L^3$ are each, --

Column 58, line 49, reads "-CF3," should read -- $-CF^3$, --

Column 58, line 50, reads "$L^4$ $L^6$ cannot" should read -- $L^4$ and $L^6$ cannot --

Column 60, line 13, reads "An Electro optical" should read -- An Electro-optical --

Signed and Sealed this

Twenty-seventh Day of July, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,291,366 B2 | Page 1 of 1 |
| APPLICATION NO. | : 10/524846 | |
| DATED | : November 6, 2007 | |
| INVENTOR(S) | : Lars Lietzau | |

It is certified that error appears in the above-identified patent and that said Letters Patent is hereby corrected as shown below:

Column 56, line 58, reads "-C=C-," should read -- -C≡C-, --

Column 58, line 5, reads "=CH-may" should read -- =CH- may --

Column 58, line 29, reads "$L^2$, $L^3$ are each," should read -- $L^2$ and $L^3$ are each, --

Column 58, line 49, reads "-CF3," should read -- $-CF_3$, --

Column 58, line 50, reads "$L^4$ $L^6$ cannot" should read -- $L^4$ and $L^6$ cannot --

Column 60, line 13, reads "An Electro optical" should read -- An Electro-optical --

This certificate supersedes the Certificate of Correction issued July 27, 2010.

Signed and Sealed this
Twelfth Day of April, 2011

David J. Kappos
*Director of the United States Patent and Trademark Office*